US009677986B1

(12) United States Patent
Baldwin et al.

(10) Patent No.: US 9,677,986 B1
(45) Date of Patent: Jun. 13, 2017

(54) AIRBORNE PARTICLE DETECTION WITH USER DEVICE

(71) Applicant: AMAZON TECHNOLOGIES, INC., Seattle, WA (US)

(72) Inventors: Leo Benedict Baldwin, San Jose, CA (US); Michael Serge Devyver, Palo Alto, CA (US); Aleksandar Pance, Saratoga, CA (US)

(73) Assignee: Amazon Technologies, Inc., Seattle, WA (US)

( * ) Notice: Subject to any disclaimer, the term of this patent is extended or adjusted under 35 U.S.C. 154(b) by 221 days.

(21) Appl. No.: 14/494,925

(22) Filed: Sep. 24, 2014

(51) Int. Cl.
| G04F 1/00 | (2006.01) |
| G01N 15/14 | (2006.01) |
| G01N 15/06 | (2006.01) |
| G01C 3/08 | (2006.01) |
| G01S 17/06 | (2006.01) |
| G01D 7/00 | (2006.01) |
| H04N 5/225 | (2006.01) |
| G06T 7/00 | (2017.01) |

(52) U.S. Cl.
CPC ............ *G01N 15/06* (2013.01); *G01C 3/08* (2013.01); *G01D 7/00* (2013.01); *G01S 17/06* (2013.01); *G06T 7/0022* (2013.01); *G06T 7/0085* (2013.01); *H04N 5/2256* (2013.01); *G01N 2015/0693* (2013.01); *G06T 2200/28* (2013.01); *G06T 2207/10004* (2013.01); *G06T 2207/10152* (2013.01)

(58) Field of Classification Search
None
See application file for complete search history.

(56) References Cited

U.S. PATENT DOCUMENTS

| 2007/0064980 A1* | 3/2007 | Knox ..................... G01N 21/53 382/128 |
| 2007/0273878 A1* | 11/2007 | Fujii .................. G01N 15/1459 356/337 |
| 2010/0180700 A1* | 7/2010 | Fjerdingstad ........ G01N 1/2035 73/865.5 |
| 2011/0058167 A1* | 3/2011 | Knox ..................... G01N 15/06 356/338 |
| 2011/0128375 A1* | 6/2011 | Vennewald .............. G01N 1/20 348/135 |
| 2011/0221889 A1* | 9/2011 | Knox ..................... G01N 21/53 348/135 |

(Continued)

Primary Examiner — Reza Aghevli
(74) Attorney, Agent, or Firm — Lindauer Law, PLLC

(57) ABSTRACT

Described are techniques and systems for determining presence of airborne particles using one or more sensors on a user device. The airborne particles include, but are not limited to, smoke resulting from combustion, dust, fog, and so forth. In one implementation, an optical proximity sensor may be used to determine a distance to an object such as a ceiling. Smoke which collects on the ceiling reflects light that is detected by the proximity sensor and results in an apparent reduction in height. A notification of this change in height may be generated. In other implementations, other techniques may be used to detect airborne particles, such as images from a camera, dedicated particular sensors, and so forth. Information about airborne particles may aid user safety. For example, an alarm may be issued indicating a potential fire or unsafe level of pollution.

20 Claims, 12 Drawing Sheets

(56) References Cited

U.S. PATENT DOCUMENTS

| | | | |
|---|---|---|---|
| 2014/0009621 A1* | 1/2014 | Tucker | G01N 15/0227 |
| | | | 348/159 |
| 2014/0050364 A1* | 2/2014 | Brueckner | G06K 9/34 |
| | | | 382/110 |
| 2015/0302728 A1* | 10/2015 | Gettings | G08B 29/181 |
| | | | 340/506 |

* cited by examiner

AIRBORNE PARTICLE DETECTION WITH USER DEVICE

BACKGROUND

User devices such as tablet computers, smartphones, personal computers, electronic book (e-book) readers, gaming consoles, set-top boxes, media players, and so forth, are ubiquitous at a variety of locations. For example, users may use or carry a user device while at work, at home, while traveling, and so forth.

Airborne particles provide information which may be useful to maintain the well-being of the user. For example, airborne particles may include smoke resulting from combustion, pollution, dust, fog, and so forth. The user may benefit from information about changes in the airborne particles, such as smoke from a fire or dangerous levels of pollution.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
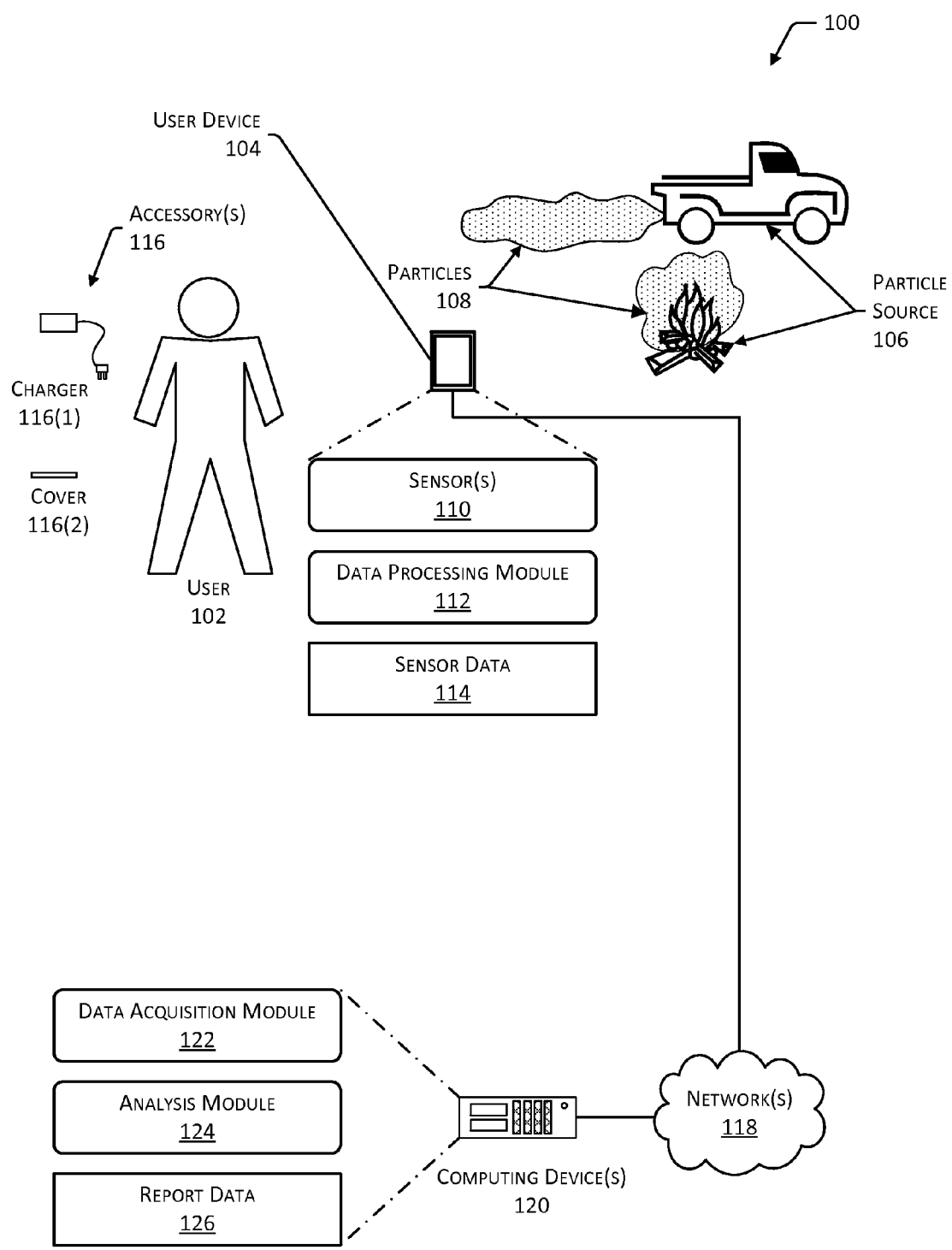
FIG. 1 is an illustrative system of a user device, such as a smartphone, tablet, set-top box, and so forth, configured to detect airborne particles.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

In a wide variety of locations and situations, a user may have one or more user devices or accessories for the user devices present. Described in this disclosure are devices and techniques to have the user devices or accessories determine information about airborne particles. The particles may result from combustion, pollution from industrial processes, dust, fog, and so forth. For example, smoke from a fire in a room comprises airborne particles. This information may be used to present or trigger a fire alarm, warn about potentially dangerous levels of pollution, and so forth. Detection of the airborne particles and determination that the density of the airborne particles exceeds a threshold value may thus provide information beneficial to the user. The devices and techniques described in this disclosure may provide an additional level of assurance or protection to the user, and may operate independently of (or in conjunction with) other detection systems such as building smoke alarms.

In some implementations, a sensor such as a particle sensor may be included in the user device or as an accessory for the user device. For example, the particle sensor may be incorporated into a charger, protective cover, and so forth. The dedicated particle sensor may use optical, ionization, or other techniques to determine presence of airborne particles. In some implementations, the particle sensor may be configured to characterize the airborne particles. The characterization of the airborne particles may include size, color, albedo, mass, chemical composition, and so forth.

Other sensors on the user device or accessory may be configurable to detect airborne particles. These sensors may also provide other functionality. In a first implementation, an optical proximity sensor may provide distance data, and during normal use of the user device, the distance data may be used to determine when the user device is close to a human body or another object. The optical proximity sensor may use time-of-flight (ToF), structured light, interferometry, coded aperture, or other techniques to generate the distance data. For example, ToF determines a propagation time (or "round-trip" time) of a pulse of emitted light from an optical emitter or illuminator and the light that is reflected or otherwise returned to an optical receiver or detector. By dividing the propagation time in half and multiplying the result by the speed of light in air, the distance to an object may be determined. In another implementation, a structured light pattern may be provided by the optical emitter. A portion of the structured light pattern may then be detected on the object using an image sensor such as a camera, and based on an apparent distance between the features of the structured light pattern, the distance may be calculated. Other techniques may also be used to determine distance to the object.

When the user device containing the optical proximity sensor is set down, the proximity sensor may scan and look for changes in distance resulting from detection of a cloud of airborne particles, such as smoke above the optical proximity sensor. Data from the proximity sensor may be used to provide information about the airborne particles.

In a second implementation, an ambient light sensor and an optical emitter (such as a light emitting diode (LED) light used to provide illumination for a camera) may be used to detect airborne particles. In this implementation, the optical emitter may be activated, and the ambient light sensor may detect reflected light from the airborne particles. Data from the ambient light sensor may be used to provide information about the airborne particles.

In a third implementation, the optical proximity sensor may be used to determine a total distance from the optical proximity sensor to a baseline object in the environment such as a wall, ceiling, or other portion of the building in which the user device containing the optical proximity sensor is located. The total distance may represent a baseline. Subsequently, should a cloud of particulates form within a field-of-view of the optical proximity sensor, a particle distance is determined. For example, the particle distance indicates a distance from the optical proximity sensor to a cloud of smoke. Because the cloud of smoke lies between the optical proximity sensor and the baseline object such as the ceiling, the particle distance is less than the total distance. In one implementation, the sensor data may indicate that the particle distance is less than the total distance, which may be deemed indicative of smoke or other airborne particles. In another implementation, an interest range which is indicative of a distance extending from the baseline object may be specified. A null zone may extend from the interest range to the optical proximity sensor. Changes in the distance within the interest range may be used to generate sensor data while changes in the null zone outside of the interest range may be disregarded. For example, where the baseline object comprises the ceiling and interest range comprises 50 centimeters (cm) extending from the ceiling towards the optical proximity sensor, smoke which accumulates within 50 cm of the ceiling may trigger an alarm while a hand moving 20 cm from the optical proximity sensor may be disregarded.

In a fourth implementation, an optical emitter such as a laser or LED is configured to generate emitted light having an emitted angle or beamwidth that traverses a portion of a field-of-view of an image sensor such as a camera. Airborne particles that are present reflect or scatter light within the beam which is then detected by the image sensor and stored in an image. By comparing ambient light from the portion of the image that does not include the beam with that portion that does, presence and other information about airborne particles may be determined. The emitted light may have a duration of less than 100 microseconds (µs), and operation of the image sensor may be configured such that the image is acquired during the emission of the light.

In the fifth implementation, images from the image sensor may be compared with one another to detect changes associated with the presence of airborne particles. For example, edges of features present in a first image may be detected and used to establish a baseline. In a subsequent image, presence of airborne particles may be determined based at least in part on the edges of the features becoming less distinct (e.g. "fuzzier") or obscured. Other image analysis techniques may also be used to determine information about airborne particles in the images. For example, a change in overall contrast or color of the image may be indicative of airborne particles such as smoke obscuring the ceiling.

In some implementations, sensor data indicative of the airborne particles may be provided to other devices such as a server for further processing. For example, the sensor data from several different devices at different locations within a facility may assist emergency responders in determining an extent of a fire.

By utilizing the devices and techniques described in this disclosure, additional information may be provided to the user or other parties who benefit from the health and well-being of the user or others. For example, the user may gain peace of mind while traveling by having a smart phone or other user device which may assist in detecting and alerting the user to an unsafe condition such as a fire.

Illustrative System

FIG. 1 is an illustrative system 100 configured to detect airborne particles. A user 102 may be present at a facility such as a dwelling, office, factory, hotel, train, and so forth. In some implementations, the facility may include a vehicle, such as an aircraft, automobile, and so forth.

The user 102 may have one or more user devices 104. The user devices 104 may include smartphones, tablet computers, electronic book (e-book) readers, televisions, personal computers, gaming consoles, set-top boxes, media players, and so forth. The user devices 104 may be configured for operation from a fixed location or may be portable. For example, the set-top boxes may be designed to plug into televisions and other devices such that they operate while in a single physical location. In another example, smartphones, tablet computers, e-book readers, and so forth, may be suitable for use in any location, while the user 102 is moving, and so forth.

The environment around the user 102 and the user device 104 may include one or more particle sources 106. The particle sources 106 may comprise chemical reactions such as combustion, industrial processes, weather (such as wind raising a dust storm), volcanic action, and so forth. The particle sources 106 produce airborne particles (particles) 108 or result in the suspension of particles in the air. For example, a fire may produce smoke comprising particles 108, while wind may produce a sandstorm in which sand is suspended in the air. The particle sources 106 may be proximate to the user 102 or may be at a great distance. For example, the particles 108 which are proximate to the user 102 and the user device 104 may originate from a cigarette held by the user 102. In another example, the particles 108 may originate from a forest fire hundreds of kilometers away.

The particles 108 may be indicative of a potential hazard to the user 102. For example, where the particle source 106 is a fire and the particles 108 are smoke, the user 102 may be at risk of danger from the heat and toxins in the smoke. In another example, where the particle source 106 is an industrial process, the user 102 may be at risk of breathing difficulties such as an asthma attack due to the particles 108.

The user device 104 may include or couple to one or more sensors 110. The sensors 110 are configured to generate information about the environment in which the user device 104 is present. For example, the sensors 110 acquire information on the physical world around the user device 104. The sensors 110 are described in more detail below with regard to FIG. 2. The data processing module 112 is coupled to the sensors 110 and is configured to generate sensor data 114. The sensor data 114 may comprise information about the particles 108. For example, the sensor data 114 may indicate characteristics of the particles 108 such as density, size, color, chemical composition, temperature, and so forth. Output from the user device 104 may be generated responsive to the sensor data 114. For example, should the sensor data 114 indicate that the particles 108 exceed a threshold value, an alarm may be presented to the user 102. One or more output devices, as discussed in more detail below with regard to FIG. 2 may present the output to the user 102. Operation of the data processing module 112 in generating sensor data 114 is discussed in more detail below with regard to FIG. 3.

One or more accessories 116(1), 116(2), . . . , 116(A) may be used in conjunction with or coupled to the user device 104. As used in this disclosure, letters in parenthesis such as "(A)" indicate an integer value. For example, an accessory charger 116(1) may be configured to provide electrical power to the user device 104 to recharge batteries internal to the user device 104. In another example, an accessory cover 116(2) may be configured to physically couple to the user device 104 to change the aesthetics of the user device 104, to provide physical protection to the user device 104, to provide additional functionality, and so forth. The accessories 116 may include one or more sensors 110. In some implementations, the accessory 116 may include a specialized sensor 110 configured to detect the particles 108.

The user device 104, the accessory 116, or both may include a connector configured to electrically couple to another device. For example, the connector may include a plug, contact, pin, and so forth. A power supply may be configured to provide electrical power to the other device using the connector. In some implementations, instead of or in addition to the connector, power may be transferred wirelessly. For example, an inductive coupling may be used to transfer energy to or from the other device.

The user device 104 may couple to one or more networks 118. The networks 118 may include public networks, private networks, or a combination thereof. The networks 118 may include, but are not limited to, personal area networks (PANs), local area networks (LANs), wide area networks (WANs), and so forth. The networks 118 may communicate using Ethernet, Wi-Fi™, Bluetooth®, ZigBee®, 3G, 4G, or other technologies.

A computing device 120 such as a server is coupled to the network 118 and is in communication with one or more of the user devices 104, other computing devices 120, other devices, and so forth. The computing device 120 may comprise one or more physical computing devices, virtual computing devices, or utilize a combination thereof. In some implementations, the computing device 120 may not require end-user knowledge of the physical location and configuration of the system that delivers the services. For example, the server computing devices 120 may be described using expressions including "on-demand computing", "software as a service (SaaS)", "platform computing", "network-accessible platform", "cloud services", "data centers", and so forth. Services provided by the computing device 120 may be distributed across one or more physical or virtual devices. The computing device 120 may include one or more modules and data including, but not limited to, a data acquisition module 122, analysis module 124, report data 126, and so forth.

The data acquisition module 122 is configured to acquire the sensor data 114 from one or more user devices 104. Information acquired by the data acquisition module 122 may then be provided to the analysis module 124. The analysis module 124 may be configured to combine sensor data 114 from a plurality of user devices 104, sensors 110, or combination thereof to generate report data 126. In some implementations, the analysis module 124 may be configured to process the sensor data 114 and return report data 126 to the corresponding user device 104 which originated the sensor data 114.

The report data 126 may comprise information such as location and geographic coverage of particles 108, location information indicative of geolocation of the user devices 104 which are provided sensor data 114, and so forth. In some implementations, the report data 126 may be provided to the users 102 or to other parties such as emergency services organizations. For example, the report data 126 may be provided to the fire department to facilitate firefighting activities and to locate users 102 who may be affected by a fire.

Figure 2:
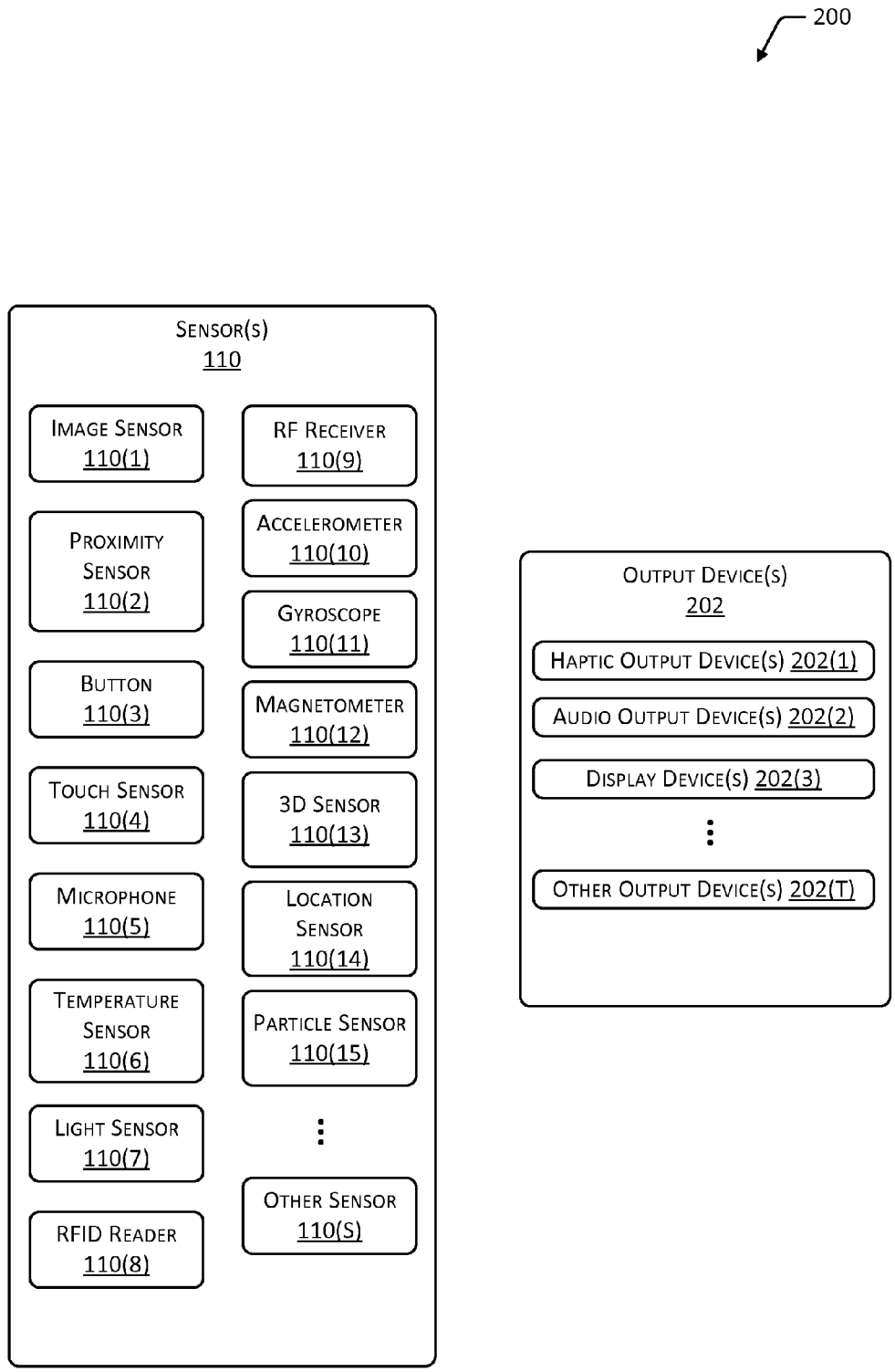
FIG. 2 illustrates a block diagram of sensors and output devices that may be used by the user device during operation.

FIG. 2 illustrates a block diagram 200 of sensors 110 and output devices 202 that may be used by the system 100 during operation. As described above, the sensors 110 may generate sensor data 114.

The one or more sensors 110 may be integrated with, or be internal to, the user device 104. For example, the sensors 110 may be built-in to the user device 104 during manufacture. In other implementations, the sensors 110 may be part of an accessory 116 or other device which is configurable to couple to the user device 104. For example, the sensors 110 may comprise a device external to the user device 104 that is in communication with the user device 104 using Bluetooth® or another wireless communication technology.

The sensors 110 may include one or more image sensors 110(1). The image sensors 110(1) may include image sensors configured to acquire images of a scene. The image sensors are configured to detect light in one or more wavelengths including, but not limited to, terahertz, infrared, visible, ultraviolet, and so forth. The image sensors may comprise charge coupled devices (CCD), complementary metal oxide semiconductor (CMOS) devices, microbolometers, and so forth.

One or more proximity sensors 110(2) are configured to determine proximity of an object. The proximity sensors 110(2) may use optical, electrical, ultrasonic, electromagnetic, or other techniques to determine a presence of an object. In some implementations, the proximity sensors 110(2) may use an optical emitter and an optical detector to determine proximity. For example, an optical emitter may emit light, a portion of which may then be reflected by the object back to the optical detector to provide an indication that the object is proximate to the proximity sensor 110(2).

In other implementations, the proximity sensors 110(2) may comprise a capacitive proximity sensor configured to provide an electrical field and determine a change in electrical capacitance due to presence or absence of an object within the electrical field.

The proximity sensors 110(2) may be configured to provide sensor data 114 indicative of one or more of a presence or absence of an object, a distance to the object, or characteristics of the object. An optical proximity sensor 110(2) may use time-of-flight (ToF), structured light, interferometry, or other techniques to generate the distance data. For example, ToF determines a propagation time (or "round-trip" time) of a pulse of emitted light from an optical emitter or illuminator that is reflected or otherwise returned to an optical detector. By dividing the propagation time in half and multiplying the result by the speed of light in air, the distance to an object may be determined. In another implementation, a structured light pattern may be provided by the optical emitter. A portion of the structured light pattern may then be detected on the object using an image sensor such as a camera, and based on an apparent distance between the features of the structured light pattern, the distance may be calculated. Other techniques may also be used to determine distance to the object. In another example, the color of the reflected light may be used to characterize the object, such as skin, wood, smoke, and so forth.

One or more buttons 110(3) are configured to accept input from the user 102. The buttons 110(3) may comprise mechanical, capacitive, optical, or other mechanisms. For example, the buttons 110(3) may comprise mechanical switches configured to accept an applied force from a touch of the user 102 to generate an input signal.

The sensors 110 may include one or more touch sensors 110(4). The touch sensors 110(4) may use resistive, capacitive, surface capacitance, projected capacitance, mutual capacitance, optical, Interpolating Force-Sensitive Resistance (IFSR), or other mechanisms to determine the position of a touch or near-touch. For example, the IFSR may comprise a material configured to change electrical resistance responsive to an applied force. The location within the material of that change in electrical resistance may indicate the position of the touch.

One or more microphones 110(5) may be configured to acquire information indicative of sound present in the environment. In some implementations, arrays of microphones 110(5) may be used. These arrays may implement beamforming techniques to provide for directionality of gain. The one or more microphones 110(5) may be used to acquire audio data, such as to determine an ambient noise level.

A temperature sensor (or thermometer) 110(6) may provide information indicative of a temperature of an object. The temperature sensor 110(6) in the user device 104 may be configured to measure ambient air temperature proximate to the user 102, the body temperature of the user 102, and so forth. The temperature sensor 110(6) may comprise a silicon bandgap temperature sensor, thermistor, thermocouple, or other device. In some implementations, the temperature sensor 110(6) may comprise an infrared detector configured to determine temperature using thermal radiation.

The sensors 110 may include one or more light sensors 110(7). The light sensors 110(7) may be configured to provide information associated with ambient lighting conditions such as a level of illumination. The light sensors 110(7) may be sensitive to wavelengths including, but not limited to, infrared, visible, or ultraviolet light.

One or more radio frequency identification (RFID) readers 110(8), near field communication (NFC) systems, and so forth, may also be included as sensors 110. The user 102, objects around the user device 104, locations within a building, and so forth, may be equipped with one or more radio frequency (RF) tags. The RF tags are configured to emit an RF signal. In one implementation, the RF tag may be a radio frequency identification (RFID) tag configured to emit the RF signal upon activation by an external signal. For example, the external signal may comprise a RF signal or a magnetic field configured to energize or activate the RFID tag. In another implementation, the RF tag may comprise a transmitter and a power source configured to power the transmitter. For example, the RF tag may comprise a Bluetooth® Low Energy (BLE) transmitter and battery. In other implementations, the RF tag may use other techniques to indicate its presence. For example, an acoustic tag may be configured to generate an ultrasonic signal which is detected by corresponding acoustic receivers. In yet another implementation, the RF tag may be configured to emit an optical signal. For example, unique RF tags storing room numbers or other location data may be located within each room of a hotel to provide location data. The RFID reader 110(8) may read this information and include the room number within the sensor data 114.

One or more RF receivers 110(9) may also be included as sensors 110. In some implementations, the RF receivers 110(9) may be part of transceiver assemblies. The RF receivers 110(9) may be configured to acquire RF signals associated with Wi-Fi™ Bluetooth®, ZigBee®, 3G, 4G, LTE, or other wireless data transmission technologies. The RF receivers 110(9) may provide information associated with data transmitted via radio frequencies, signal strength of RF signals, and so forth. For example, information from the RF receivers 110(9) may be used to facilitate determination of a location of the user device 104.

The sensors 110 may include one or more accelerometers 110(10). The accelerometers 110(10) may provide information such as the direction and magnitude of an imposed acceleration. Data such as rate of acceleration, determination of changes in direction, speed, and so forth, may be determined using the accelerometers 110(10).

A gyroscope 110(11) provides information indicative of rotation of an object affixed thereto. For example, the gyroscope 110(11) may indicate whether the user device 104 has been rotated.

A magnetometer 110(12) may be used to determine an orientation by measuring ambient magnetic fields, such as the terrestrial magnetic field. For example, output from the magnetometer 110(12) may be used to determine whether the device containing the sensor 110, such as the user device 104 or the accessory 116, has changed orientation or otherwise moved.

One or more 3D sensors 110(13) may also be included in the sensors 110. The 3D sensors 110(13) are configured to acquire spatial or three-dimensional data, such as distance, 3D coordinates, point cloud, and so forth, about objects within a sensor field-of-view. The 3D sensors 110(13) may include range cameras, lidar systems, sonar systems, radar systems, structured light systems, stereo vision systems, optical interferometry systems, and so forth.

A location sensor 110(14) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 110(14) may include, but is not limited to, radio navigation-based systems such as terrestrial or satellite-based navigational systems. The satellite-based navigation system may include one or more of a Global Positioning System (GPS) receiver, a global navigation satellite system (GLONASS) receiver, a Galileo receiver, an Indian Regional Navigational Satellite System, and so forth. In some implementations, the location sensor 110(14) may be omitted or operate in conjunction with an external resource such as a cellular network operator providing location information.

A particle sensor 110(15) is configured to provide information about particles 108. The particle sensor 110(15) may utilize optical, electrical, or other techniques to determine information about particles 108. For example, the particle sensor 110(15) may emit light and look for reflections or other optical interactions between particles 108 and the emitted light. In another example, the particle sensor 110(15) may include an ionization source and at least a pair of electrodes used to determine whether a current is flowing as a result of ionized particles 108. Several implementations of particle sensors 110(15) which use optical techniques are described in at least a portion of the following figures.

The sensors 110 may include other sensors 110(S) as well. For example, the other sensors 110(S) may include barometric sensors, hygrometers, biomedical sensors, and so forth. For example, the biomedical sensors may be configured to measure one or more of brain waves, muscle activity, pulse, respiration, galvanic skin response, pupillary dilation, and so forth.

In some implementations, the sensors 110 may include hardware processors, memory, and other elements configured to perform various functions. Furthermore, the sensors 110 may be configured to communicate by way of the network 118 or may couple directly with the user device 104.

The user device 104 may include or may couple to one or more output devices 202. The output devices 202 are configured to generate signals which may be perceived by the user 102, detectable by the sensors 110, or a combination thereof.

Haptic output devices 202(1) are configured to provide a signal which results in a tactile sensation to the user 102. The haptic output devices 202(1) may use one or more mechanisms such as electrical stimulation or mechanical displacement to provide the signal. For example, the haptic output devices 202(1) may be configured to generate a modulated electrical signal which produces an apparent tactile sensation in one or more fingers of the user 102. In another example, the haptic output devices 202(1) may comprise piezoelectric or rotary motor devices configured to provide a vibration which may be felt by the user 102.

One or more audio output devices 202(2) are configured to provide acoustic output. The acoustic output includes one or more of infrasonic sound, audible sound, or ultrasonic sound. The audio output devices 202(2) may use one or more mechanisms to generate the acoustic output. These mechanisms may include, but are not limited to: voice coils, piezoelectric elements, magnetorestrictive elements, electrostatic elements, and so forth. For example, a piezoelectric buzzer or a speaker may be used to provide acoustic output.

The display devices 202(3) may be configured to provide output which may be seen by the user 102 or detected by a light-sensitive detector such as the image sensor 110(1) or light sensor 110(7). The output may be monochrome or color. The display devices 202(3) may be emissive, reflective, or both. An emissive display device 202(3), such as using LEDs, is configured to emit light during operation. In comparison, a reflective display device 202(3), such as using an electrophoretic element, relies on ambient light to present an image. Backlights or front lights may be used to illuminate non-emissive display devices 202(3) to provide visibility of the output in conditions where the ambient light levels are low.

The display mechanisms may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, and so forth. These display mechanisms are configured to emit light, modulate incident light emitted from another source, or both. The display devices 202(3) may operate as panels, projectors, and so forth.

The display devices 202(3) may be configured to present images. For example, the display devices 202(3) may comprise a pixel-addressable display. The image may comprise at least a two-dimensional array of pixels or a vector representation of an at least two-dimensional image.

In some implementations, the display devices 202(3) may be configured to provide non-image data, such as text characters, colors, and so forth. For example, a segmented electrophoretic display device 202(3), segmented LED, and so forth, may be used to present information such as letters or numbers. The display devices 202(3) may also be configurable to vary the color of the segment, such as using multicolor LED segments.

Other output devices 202(T) may also be present. For example, the other output devices 202(T) may include scent/odor dispensers, document printers, three-dimensional printers, and so forth.

In some implementations, the output devices 202 may be used to provide a notification or alarm to the user 102. For example, the audio output device 202(2) may be configured to emit a siren sound to alert the user 102 of a possible fire as a result of sensor data 114 indicating the airborne particles 108 comprising smoke have exceeded a threshold level.

Figure 3:
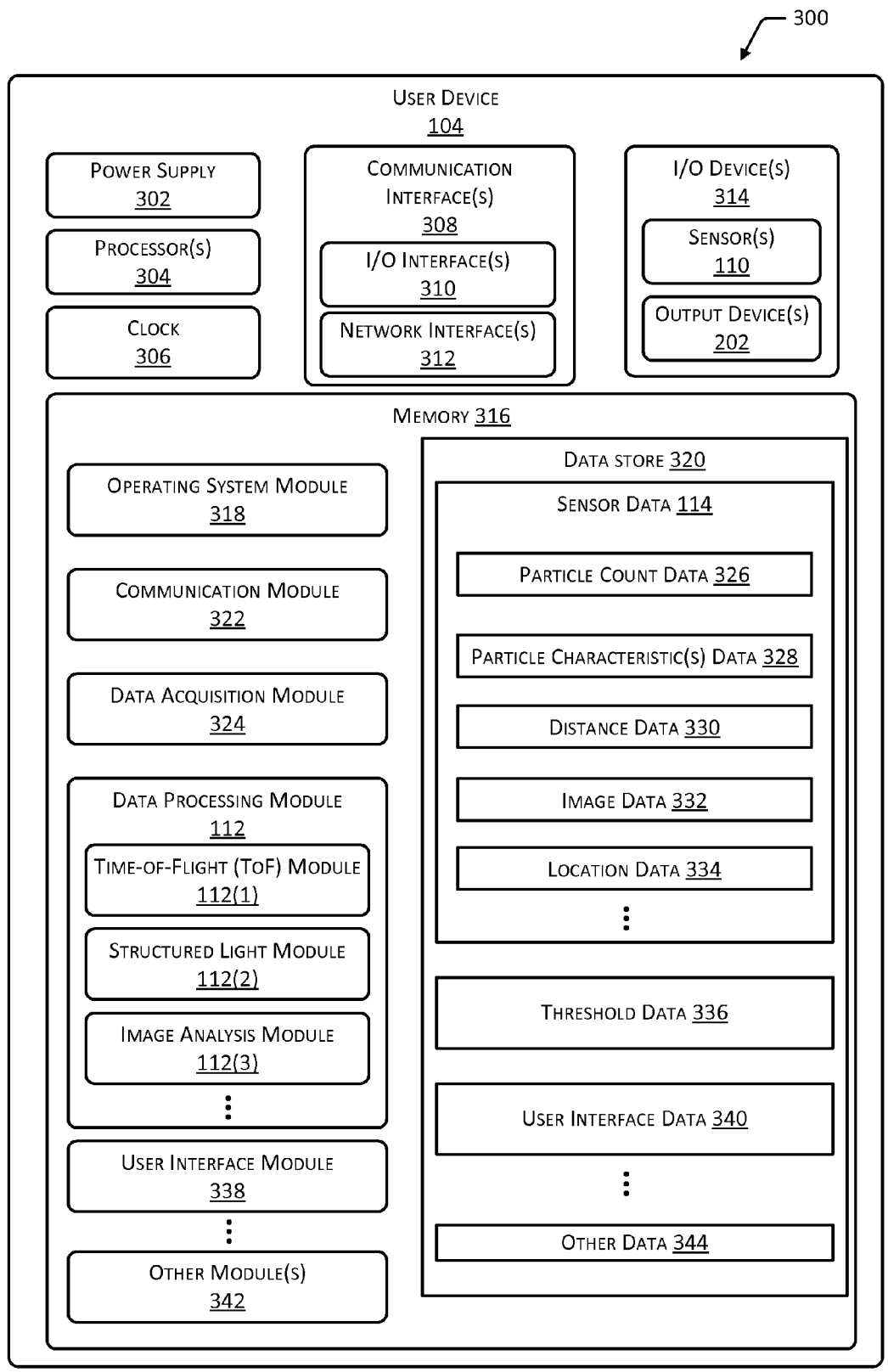
FIG. 3 illustrates a block diagram of the user device configured to use one or more sensors to detect airborne particles.

FIG. 3 illustrates a block diagram 300 of the user device 104 configured to support operation of the system 100.

One or more power supplies 302 are configured to provide electrical power suitable for operating the components in the user device 104. In some implementations, the power supply 302 may comprise a rechargeable battery, fuel cell, photovoltaic cell, power conditioning circuitry, and so forth.

The user device 104 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, determine a propagation delay of an emitted signal, and so forth.

The user device 104 may include one or more communication interfaces 308 such as I/O interfaces 310, network interfaces 312, and so forth. The communication interfaces 308 enable the user device 104, or components thereof, to communicate with other devices or components. The communication interfaces 308 may include one or more I/O interfaces 310. The I/O interfaces 310 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 310 may couple to one or more I/O devices 314. The I/O devices 314 may include input devices such as one or more of a sensor 110, keyboard, mouse, scanner, and so forth. The I/O devices 314 may also include output devices 202 such as one or more of a display, printer, audio speakers, and so forth. In some embodiments, the I/O devices 314 may be physically incorporated with the user device 104 or may be externally placed.

The network interfaces 312 are configured to provide communications between the user device 104 and other devices, such as the sensors 110, routers, access points, computing devices 120, and so forth. The network interfaces 312 may include devices configured to couple to PANs, LANs, WANs, and so forth. For example, the network interfaces 312 may include devices compatible with Ethernet, Wi-Fi™, Bluetooth®, ZigBee®, 3G, 4G, LTE, and so forth.

The user device 104 may also include one or more busses or other internal communications hardware or software that allow for the transfer of data between the various modules and components of the user device 104.

As shown in FIG. 3, the user device 104 includes one or more memories 316. The memory 316 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 316 provides storage of computer-readable instructions, data structures, program modules, and other data for the operation of the user device 104. A few example functional modules are shown stored in the memory 316, although the same functionality may alternatively be implemented in hardware, firmware, or as a system on a chip (SOC).

The memory 316 may include at least one operating system (OS) module 318. The OS module 318 is configured to manage hardware resource devices such as the I/O interfaces 310, the network interfaces 312, the I/O devices 314, and provide various services to applications or modules executing on the processors 304. The OS module 318 may implement a variant of the FreeBSD™ operating system as promulgated by the FreeBSD Project; other UNIX™ or UNIX-like operating system; a variation of the Linux™ operating system as promulgated by Linus Torvalds; the Windows® operating system from Microsoft Corporation of Redmond, Wash., USA; or other operating systems.

Also stored in the memory 316 may be a data store 320 and one or more of the following modules. These modules may be executed as foreground applications, background tasks, daemons, and so forth. The data store 320 may use a flat file, database, linked list, tree, executable code, script, or other data structure to store information. In some implementations, the data store 320 or a portion of the data store 320 may be distributed across one or more other devices including the computing devices 120, network attached storage devices, and so forth.

A communication module 322 may be configured to establish communications with one or more of other user devices 104, computing devices 120, the sensors 110, or other devices. The communications may be authenticated, encrypted, and so forth.

The memory 316 may also store a data acquisition module 324 and the data processing module 112. The data acquisition module 324 is configured to acquire sensor data 114 from the one or more sensors 110. In some implementations, the data acquisition module 324 may perform some processing of the sensor data 114. For example, values indicative of an intensity of a signal produced by a particle sensor 110(15) may be converted into a value indicative of a concentration of airborne particles 108.

The data processing module 112 is configured to generate sensor data 114. In some implementations, the data processing module 112 may also perform one or more actions responsive to the sensor data 114. For example, upon determining that the concentration of airborne particles 108 exceeds a threshold value, the data processing module 112 may issue a notification or generate an alarm using one or more of the output devices 202.

The sensor data 114 may be stored in the data store 320 and may include one or more of particle count data 326, particle characteristic data 328, distance data 330, image data 332, location data 334, or threshold data 336. The sensor data 114 may be generated by one or more of the sensor 110, the data acquisition module 324, the data processing module 112, and so forth.

The particle count data 326 is indicative of a count of particles 108 detected per interval of time, number of particles 108 per unit volume, change in presence of particles 108 from a first time to a second time, and so forth. For example, the particle count data 326 may indicate that there are more than 200 particles per milliliter detected.

The particle characteristic data 328 may be indicative of one or more of size, color, chemical composition, temperature, and so forth. For example, the particle characteristic data 328 may indicate that the particles 108 have a size exceeding 10 microns (µ) and a temperature of 280° C.

The distance data 330 comprises information indicative of a distance between the sensor 110 and a detected object. The detected object may comprise the user 102 or a portion thereof, something in the environment such as a wall or ceiling, airborne particles 108 such as a cloud of smoke, and so forth. The distance data 330 may be expressed in terms of a linear measurement or a time interval with respect to a velocity of a signal, such as light. For example, the distance data 330 may be expressed in terms of meters or nanoseconds. Continuing the example, given that the speed of an optical signal in air is approximately 2.99705E8 m/s, the distance data 330 may be expressed as 1 meter (m) or approximately 3.44 nanoseconds (ns).

The image data 332 comprises information indicative of images acquired from one or more of the image sensors 110(1). The image data 332 may comprise individual still images, video images, or a combination thereof.

The location data 334 provides information indicative of a location of one or more of the user 102, the user device 104, the accessory 116, and so forth. For example, the location data 334 may indicate the latitude and longitude of the user device 104, room number in a hotel, and so forth. Furthermore, in some implementations, the location data 334 may indicate where the user 102 is in relation to the user device 104. For example, the location data 334 may indicate that the user 102 is approximately 3 meters north of the user device 104. The location data 334 may be generated using information from the location sensor(s) 110(14).

The data processing module 112 may be configured to acquire input from the one or more sensors 110 and generate sensor data 114. The data processing module 112 may use one or more signal processing or data analysis techniques. For example, the data processing module 112 may acquire multiple inputs from a single sensor 110 over a span of time and determine the sensor data 114 as an average of those multiple inputs.

The data processing module 112 may be configured to generate sensor data 114 using one or more of a time-of-flight (ToF) module 112(1), structured light module 112(2), image analysis module 112(3), or other module 112(D). The time-of-flight module 112(1) and the structured light module 112(2) may be configured to generate distance data 330 indicative of a distance between the sensor 110 and an object. The ToF module 112(1) is configured to use propagation time which is indicative of an amount of time an emitted signal takes to travel from an emitter to a detector. For example, the ToF module 112(1) determines a propagation time (or "round-trip" time) of a pulse of emitted light from an optical emitter or illuminator that is reflected or otherwise returned to a detector. By dividing the propagation time in half and multiplying the result by the speed of light in air, the distance to an object may be determined.

In some implementations, the sensor 110 may include hardware configured to determine the distance data 330. For example, an optical proximity sensor 110(2) may include circuitry configured to determine an elapsed time between emission of light by the one or more optical emitters and detection of the light by the one or more optical receivers. Continuing the example, the optical proximity sensor 110(2) may include circuitry configured to calculate a distance based on the elapsed time.

The structured light module 112(2) uses a structured light pattern provided by the optical emitter. For example, the structured light pattern may comprise a regular pattern such as a grid, a pseudorandom noise "speckle" pattern, and so forth. The pattern comprises one or more features at known locations relative to one another within the pattern. The structured light pattern is projected onto the scene, such as from the optical emitter of the 3D sensor 110(13). An image sensor 110(1) acquires an image which includes at least a portion of the pattern. The portion of the pattern in the image is detected on a surface of an object. Based on an apparent distance between the features of the structured light pattern, the distance data 330 between the 3-D sensor 110(13) and the object may be calculated.

The image analysis module 112(3) may be used to process the image data 332 to determine information about the airborne particles 108. Image analysis module 112(3) may be configured to generate particle count data 326, particle characteristic data 328, and so forth. The image analysis module 112(3) may be configured to activate an optical emitter such as an LED or laser to provide illumination, acquire or access image data 332, and analyze the image data 332 to generate sensor data 114.

In one implementation, an optical emitter such as a laser or LED is configured to generate emitted light having an emitted angle or beamwidth which traverses a portion of a field-of-view of an image sensor 110(1) such as a camera. Should airborne particles 108 be present in the environment, they reflect or scatter light within the beam which is then detected by the image sensor 110(1). The image data 332 which includes the image of the emitted light being reflected provides information indicative of airborne particles 108. By comparing the portion of the image data 332 that is associated with the ambient light from the portion of the image data 332 that does not include the beam with the portion that does, presence and other information about airborne particles 108 may be determined and effects from ambient light are reduced or eliminated.

The emitted light from an optical emitter may be emitted as one or more pulses having a duration of less than 100 microseconds (μs). The data processing module 112 may coordinate operation of the optical emitter and the image sensor 110(1). For example, the image sensor 110(1) may be configured to acquire image data 332 while the beam of light is being emitted from the LED or the laser.

In another implementation, image data 332 comprising several images acquired by the image sensor 110(1) may be compared with one another to detect changes associated with the presence of airborne particles 108. For example, edges of features present in first image data 332(1) may be detected and used to establish a baseline. In subsequent image data 332(2), presence of airborne particles 108 may be determined based at least in part on the edges of the features becoming less distinct or obscured. Other image analysis techniques may also be used to determine information about airborne particles 108 in the image data 332. For example, a change in overall contrast or color of the image may be indicative of airborne particles 108 such as smoke obscuring the ceiling.

In one implementation, the least a portion of the image processing may be performed at least in part by using one or more tools available in the OpenCV library as developed by Intel Corporation of Santa Clara, Calif., USA; Willow Garage of Menlo Park, Calif., USA; and Itseez of Nizhny Novgorod, Russia, with information available at www.opencv.org. For example, the OpenCV library may be used to detect an edge in the image data 332, characterize changes to the edge across a plurality of images, and so forth.

The data processing module 112 may access threshold data 336 stored in the data store 320. The threshold data 336 may specify one or more threshold values associated with airborne particles 108. For example, the threshold data 336 may specify a minimum level of reflected light to be detected by the optical particle sensor 110(15) that will result in an alarm. In another example, the threshold data 336 may specify a threshold value or range of values of reflectivity, as measured by an optical proximity sensor 110(2), that are associated with the presence of airborne particles 108. In yet another example, the threshold data 336 may specify an interest range distance, a minimum distance threshold, and so forth. The threshold data 336 is discussed in more detail below with regard to FIG. 9.

The data processing module 112 may compare or otherwise process the sensor data 114 from one or more sensors 110 with regard to the threshold data 336. Based at least in part on this processing, the data processing module 112 may perform one or more actions. These actions may include instructions to a user interface module 338 stored in the memory 316 to generate user interface data 340. The user interface data 340 is configured to operate the output devices 202 to generate output which may be perceptible to the user 102. For example, the data processing module 112 may determine that the concentration of airborne particles 108 exceeds a threshold value specified by threshold data 336 and instructs the user interface module 338 to generate a siren sound from an audio output device 202(2), flash a light, present a message on the display device 202(3), and so forth.

In some implementations, the user interface data 340 may be configured to present a prompt to the user 102. For example, the prompt may comprise an audio or visual presentation of "Is there a fire?". A timeout interval may be specified such that should the user 102 fail to respond to the prompt within the timeout interval, an alarm or notification may be generated.

The data processing module 112 may use input from one or more sensors 110 to determine what action, if any, to take. For example, the data processing module 112 may use information such as temperature data from the temperature sensor 110(6) exceeding a threshold temperature and distance data 330 such as determined by an optical proximity sensor 110(2) indicating a change within an interest range to generate an alarm indicative of a fire. In another example, the data processing module 112 may use the distance data 330 and the image data 332 to provide information indicative of the particles 108.

In some implementations, the data processing module 112 may use information from sensors 110 to determine that the user device 104, the accessory 116, or other device which includes at least a portion of the one or more sensors 110 has remained stationary. For example, the ToF module 112(1) and the image analysis module 112(3) may benefit from information indicating that the optical proximity sensor 110(2) or the image sensor 110(1), respectively, have not moved between measurements. The data processing module 112 may use information from one or more of the accelerometer 110(10), the gyroscope 110(11), the magnetometer 110(12), the location sensor 110(14), and so forth, to determine movement. For example, a change in magnetic field vectors as measured by the magnetometer 110(12) may indicate movement of the magnetometer 110(12).

Information about movement of the sensor 110 may thus be used to reduce or eliminate generation of erroneous sensor data 114 from the inputs of other sensors 110. Continuing the example where the sensors 110 are integrated into the user device 104, indication of movement of the user device 104 may result in the image analysis module 112(3) discarding previously acquired image data 332 and acquiring a new baseline. In some implementations, the activation of sensors 110, the generation of sensor data 114, or both may be responsive to an indication that the user device 104 has remained stationary for a threshold interval of time, or following an event such as the user 102 locking the user device 104. For example, the data processing module 112 may not begin generating sensor data 114 indicative of the particles 108 until the user device 104 has been stationary for at least two minutes.

Other modules 342 may also be present in the memory 316, as well as other data 344 in the data store 320. For example, the other modules 342 may include an audio characterization module configured to detect sounds associated with combustion and so forth. The other data 344 may include user alarm preferences and so forth. For example, the user 102 may specify low, medium, or high levels of sensitivity with regard to whether to generate an alarm responsive to the airborne particles 108.

Figure 4:
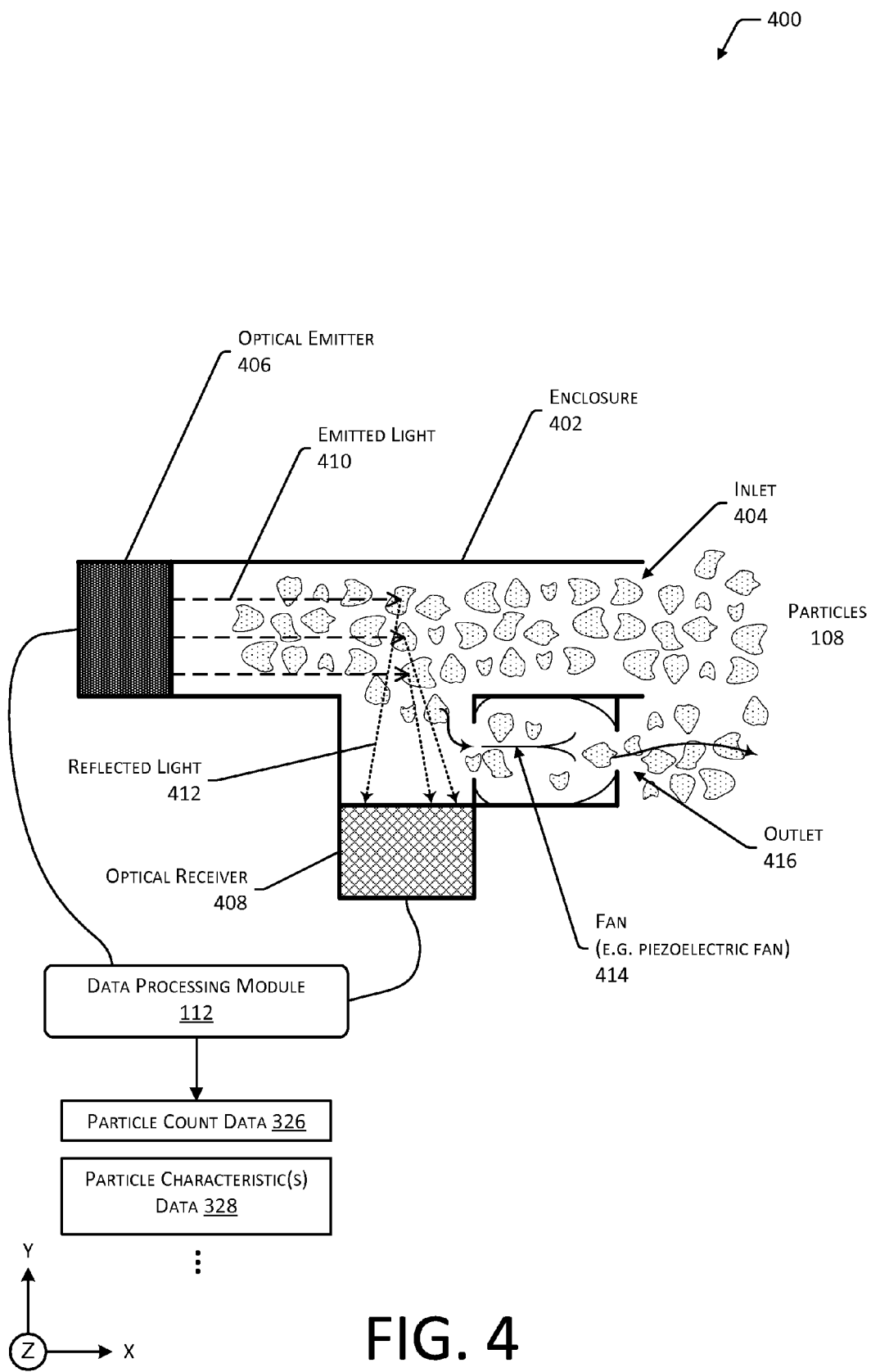
FIG. 4 illustrates a first configuration of a particle sensor configured to detect airborne particles.

FIG. 4 illustrates a first configuration 400 of a particle sensor 110(15) configured to detect airborne particles 108. The particle sensors 110(15) described in this disclosure may be incorporated into the user device 104, the accessory 116, or comprise a standalone unit.

The first configuration 400 may comprise an enclosure 402. The enclosure 402 may comprise one or more of a metal, a plastic, a ceramic, a composite, or other material. An inlet 404 is configured to admit at least a portion of the particles 108 which are suspended in the ambient air. In some implementations, the inlet 404 may include a valve, gate, door, or other feature configured to close the inlet 404. Coupled to the enclosure 402 is an optical emitter 406 and an optical receiver 408. The optical emitter 406 operates as a light source, comprising one or more devices configured to generate emitted light 410. The optical emitter 406 may comprise an LED, a laser, an incandescent lamp, a quantum dot, an electroluminescent element, a fluorescent light, and so forth. The emitted light 410 may comprise coherent light or incoherent light. The optical emitter 406 may include one or more optical components such as lenses, mirrors, diffraction gratings, shutters, polarizers, and so forth. In some implementations, the emitted light 410 may be focused or collimated.

The emitted light 410 passes through at least a portion of the enclosure 402. Should the ambient air be free from particles 108, the emitted light 410 may pass to a wall of the enclosure 402. The walls of the enclosure 402 may be absorptive of the wavelengths of the emitted light 410. For example, the enclosure 402 may comprise black plastic. Should the emitted light 410 encounter a particle 108, at least a portion of the emitted light 410 may interact with the particles 108. The interaction may include reflection, diffraction, absorption and subsequent fluorescence, and so forth. For example, the emitted light 410 may be scattered by one or more of the particles 108 such that reflected light 412 is directed toward the optical receiver 408.

The optical receiver 408 is configured to detect incident light of one or more wavelengths. The optical receiver 408 may comprise a photodiode, photomultiplier, charge coupled device (CCD), complementary metal oxide device (CMOS), and so forth. In some implementations, the image sensor 110(1) may be used as the optical receiver 408. The output from the image sensor 110(1) in this implementation may or may not be in an image. The optical emitter 406 and the optical receiver 408 may be coupled to the data processing module 112. The data processing module 112 may be configured to generate sensor data 114, such as particle count data 326, particle characteristic data 328, and so forth.

The optical emitter 406 and the optical receiver 408 may be configured to emit and detect, respectively, light in one or more wavelengths. For example, the optical emitter 406 and the optical receiver 408 may be configured to operate at one or more of infrared, visible, or ultraviolet wavelengths. In some implementations, multiple wavelengths may be used to reduce false positives, improve detection of different types of particles 108, to characterize the particles 108, and so forth.

In this implementation, the optical emitter 406 and the optical receiver 408 are oriented at a right angle to one another. For example, the optical emitter 406 is configured to emit the emitted light 410 generally along an x-axis, while the optical receiver 408 is configured to detect reflected light 412 which is traveling generally along a perpendicular y-axis.

To facilitate the flow of air containing the particles 108 through the enclosure 402, a fan 414 may be configured to draw air through the enclosure 402. For example, the fan 414 may comprise a piezoelectric fan which moves back-and-forth responsive to an application of a voltage and thus displaces air. The fan 414 may comprise a rotary motor or other mechanism to displace air. In some implementations electrostatic differentials may be used to move air without moving parts. An outlet 416 may be provided to vent air moved by the fan 414. As with the inlet 404, the outlet 416 may be configured with one or more of a gate, door, valve, and so forth. In another implementation, the outlet 416 may be placed elsewhere within the enclosure 402 to permit a flow of air within the enclosure 402.

In some implementations, instead of or in addition to the use of the optical emitter 406 and the optical receiver 408, an ionization source and two or more electrically charged plates may be used to detect the particles 108. For example, the ionization source may comprise a radioisotope such as americium-241.

Figure 5:
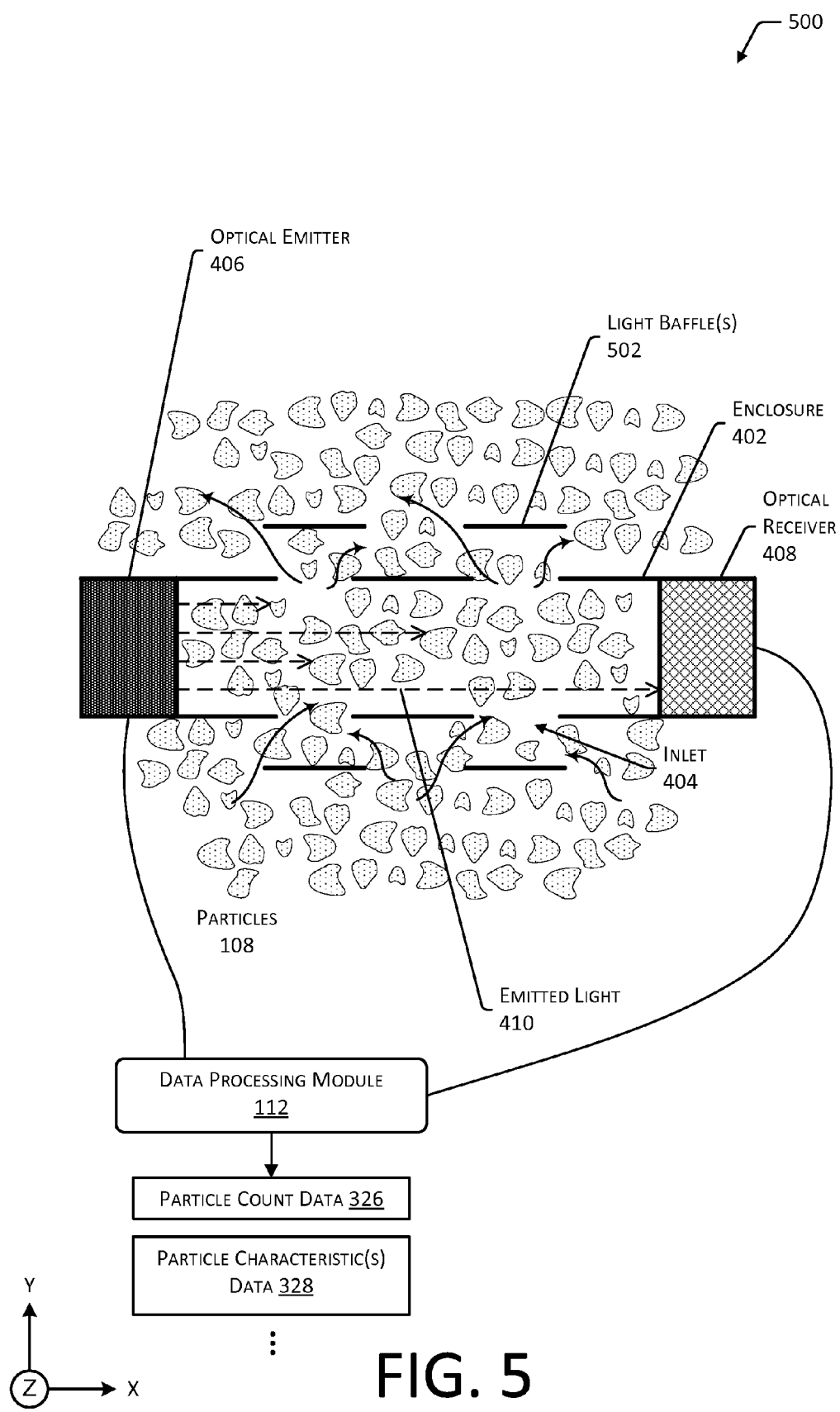
FIG. 5 illustrates a second configuration of a particle sensor configured to detect airborne particles.

FIG. 5 illustrates a second configuration 500 of the particle sensor 110(15) configured to detect airborne particles 108. Similar to the configuration described above with respect to FIG. 4, particle sensor 110(15) may include an enclosure 402, an optical emitter 406, an optical receiver 408, and the particle sensor 110(15) may be coupled to the data processing module 112.

In this configuration, the optical emitter 406 is configured to direct emitted light 410 towards the optical receiver 408 or portion thereof. In this arrangement, the optical emitter 406 generates the emitted light 410. Based at least in part on the number of particles 108 within the enclosure 402, the size of the particles 108, or other characteristics of the particles 108, the quantity of emitted light 410 which is detected at the optical receiver 408 may vary. For example, while the air is clear and no particles 108 are present, the optical receiver 408 may receive a strong signal indicative of the emitted light 410 traveling unimpeded thereto. In comparison, as smoke or other particles 108 is present within the enclosure 402, transmission of the emitted light 410 is impaired, and a corresponding signal strength provided by the optical receiver 408 decreases relative to the unimpeded scenario. To reduce or eliminate interference from ambient light which may enter the enclosure 402, one or more light baffles 502 may be positioned proximate to the inlets 404. The light baffles 502 are configured to absorb or reflect away ambient light to prevent entry into the enclosure 402.

In this configuration, openings in the enclosure 402 such as inlets 404 and outlets 416 may be provided. The openings may be configured such that they are opposite one another, diagonal from one another, and so forth.

Figure 6:
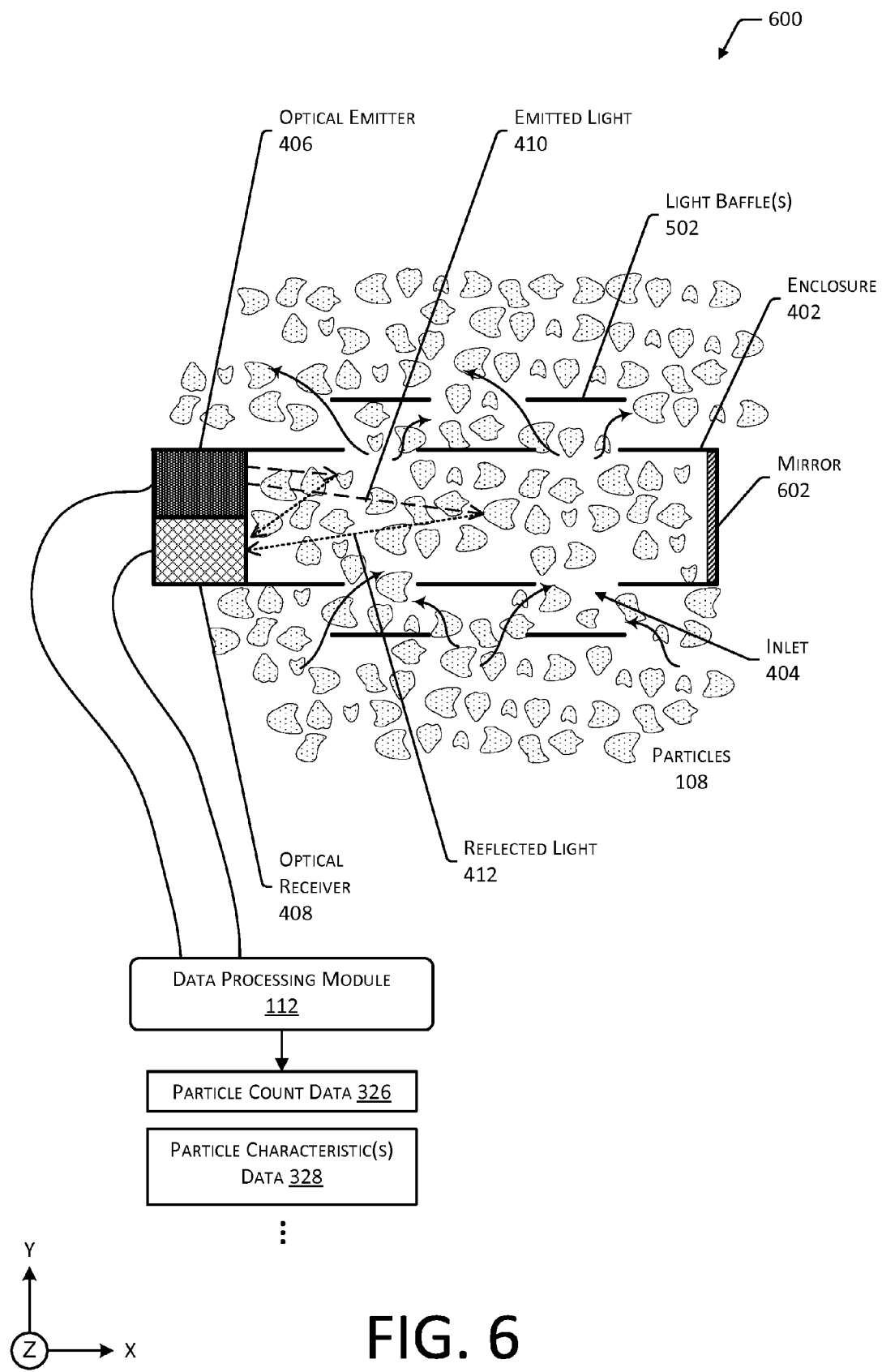
FIG. 6 illustrates a third configuration of a particle sensor configured to detect airborne particles.

FIG. 6 illustrates a third configuration 600 of the particle sensor 110(15) configured to detect the airborne particles 108. Similar to the configuration described above with respect to FIG. 4 and FIG. 5, a particle sensor 110(15) may include an enclosure 402, an optical emitter 406, an optical receiver 408, one or more light baffles 502, and the particle sensor 110(15) may be coupled to the data processing module 112.

In this configuration, as depicted, the optical emitter 406 and the optical receiver 408 may be arranged adjacent to one another along a common side or edge of the enclosure 402. With this configuration, the optical emitter 406 projects emitted light 410 into the enclosure 402. Should particles 108 be present, reflected light 412 may be directed toward the optical receiver 408. During operation, the third configuration 600 may operate similar to the first configuration 400 as described above with regard to FIG. 4. For example, an increase in the intensity or quantity of reflected light 412 detected by the optical receiver 408 may be indicative of an increase in the number of particles 108 present.

In another implementation, a mirror 602 or other material which is reflective of the emitted light 410 may be arranged at an opposite end of the enclosure 402. For example, the mirror 602 may comprise a thin film of aluminum or another metal, paint, and so forth. In this implementation, the emitted light 410 may be reflected by the mirror 602 and detected by the optical receiver 408. During operation, this implementation may be similar to that described above with regard to the second configuration 500 such that a decrease in the intensity of the reflected light 412 may be indicative of an increase in the number of particles 108. In another implementation of the configuration 600, the interior of the enclosure 402 may comprise a reflective material such as the mirror 602. However, the exterior of the enclosure 402 as well as the light baffles 502 may remain absorptive of wavelengths of light used by the optical emitter 406 and the optical receiver 408.

In some implementations, transmittance measurements obtained by measuring attenuation of emitted light 410 emitted from the optical emitter 406 and received by the optical receiver 408 may be compared with other measurements such as those of reflected light 412. A ratio or other comparison between these different measurements may be used to generate the particle count data 326, particle characteristic data 328, and so forth.

Figure 7:
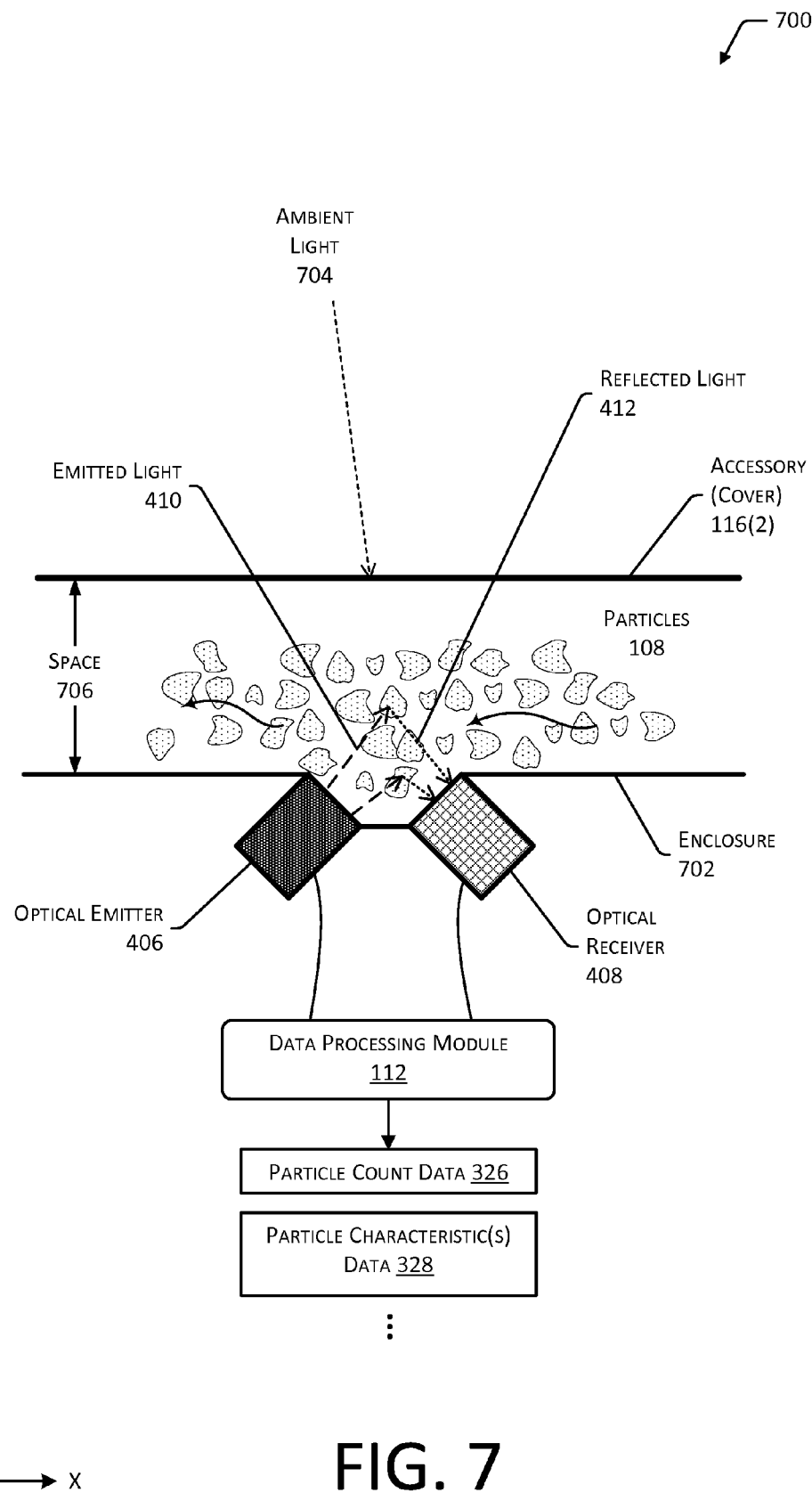
FIG. 7 illustrates a fourth configuration of a particle sensor configured to detect airborne particles.

FIG. 7 illustrates a fourth configuration 700 of a particle sensor 110(15) configured to detect the airborne particles 108. Similar to the configuration described above with respect to FIG. 4, a particle sensor 110(15) may include an enclosure 402, an optical emitter 406, an optical receiver 408, and the particle sensor 110(15) may be coupled to the data processing module 112.

In this configuration, the optical emitter 406 and the optical receiver 408 are each configured at an angle with respect to a surface of an enclosure 702. The emitted light 410 from the optical emitter 406 is projected into a volume which is beyond the surface of the enclosure 702. The optical receiver 408 is configured to detect reflected light 412 from a least a portion of this volume beyond the surface of the enclosure 702. Similar to the techniques described above, the presence of one or more particles 108 may result in reflected light 412 being directed to the optical receiver 408.

To improve performance and situations where the emitted light 410 may have the same or a similar wavelength with respect to ambient light 704, a light baffle may be provided by a cover, such as the accessory cover 116(2). In this configuration, the optical emitter 406 and the optical receiver 408 may be arranged on a front face of the user device 104. Upon closure of the accessory cover 116(2) such that the optical emitter 406 and the optical receiver 408 are obscured from ambient light 704, the data processing module 112 may be configured to have the optical emitter 406 generate emitted light 410. The data processing module 112 may then receive information indicative of reflected light 412 as received by the optical receiver 408. A space 706 is formed between the surface of the enclosure 702 and the accessory cover 116(2). The particles 108 may be moved by ambient air through the space 706. In some implementations, a fan 414 or other active element may be configured to move the ambient air. In some implementations, the interior portion of the accessory cover 116(2) proximate to the optical emitter 406 and the optical receiver 408 may be reflective or not absorptive. For example, the interior of the accessory cover 116(2) may comprise a white plastic, deposited aluminum coating, and so forth.

Figure 8:
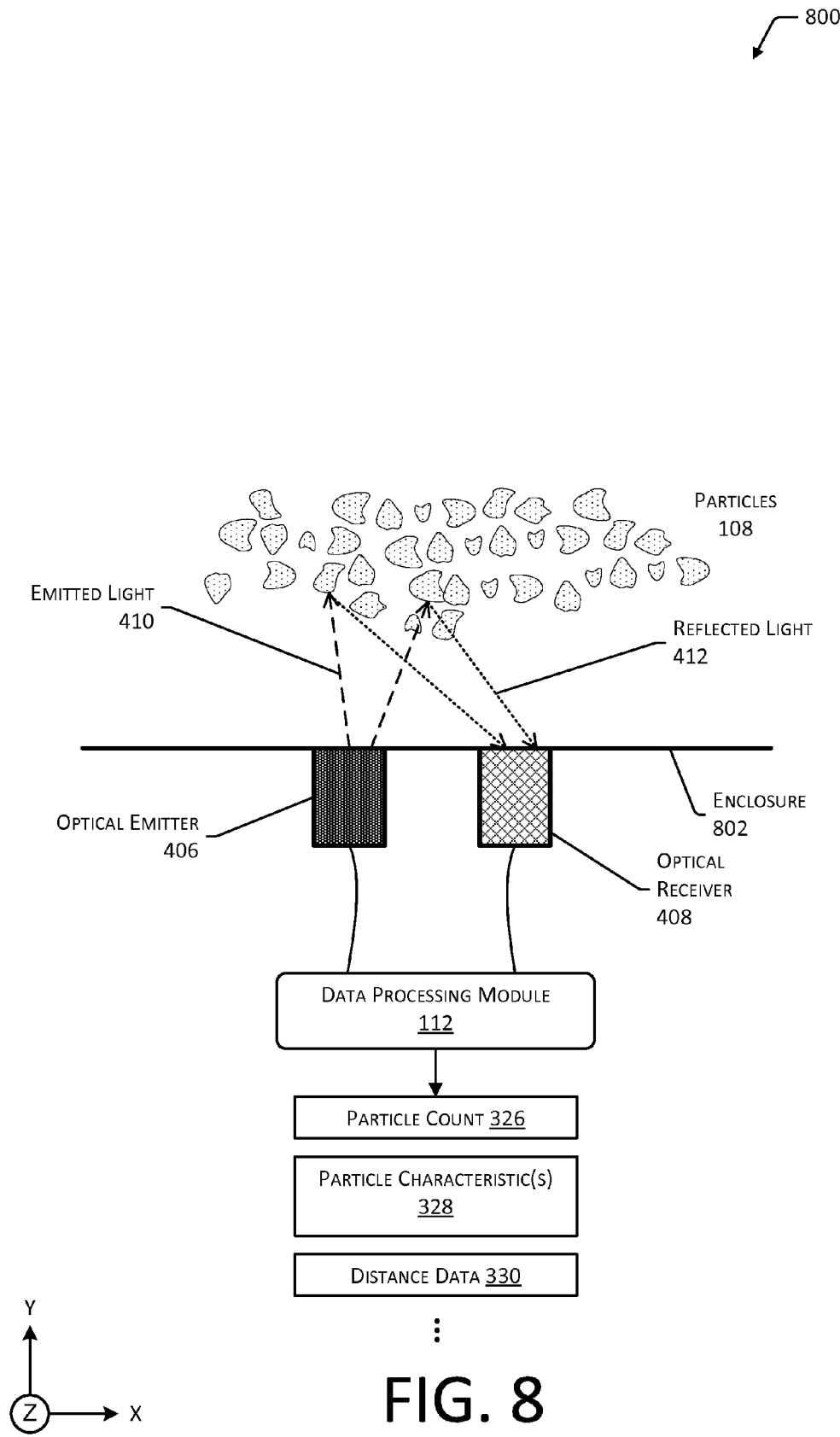
FIG. 8 illustrates an optical proximity sensor/ambient light sensor configured to detect airborne particles.

FIG. 8 illustrates a configuration 800 of an optical proximity sensor 110(2), or an ambient light sensor 110(7) operating in conjunction with an optical emitter 406, configured to detect airborne particles 108. As described above, the optical proximity sensor 110(2) may be configured to generate emitted light 410 and receive reflected light 412 as reflected by an object. For example, the optical emitter 406 may generate emitted light 410 at an infrared wavelength, while the optical receiver 408 may comprise an infrared photodiode. The optical proximity sensor 110(2) may be used for multiple purposes such as determination of proximity of the user 102 as well as the determination of presence or absence of airborne particles 108. The optical emitter 406 and the optical receiver 408 are configured to send emitted light 410 and receive reflected light 412 beyond an enclosure 802.

The determination of proximity by the optical proximity sensor 110(2) of an object may be binary such as "present" or "not present". In some implementations, the optical proximity sensor 110(2) may generate distance data 330 indicative of a distance between the optical proximity sensor 110(2) and the object(s) detected.

The optical proximity sensor 110(2) may determine proximity based on changes in amplitude of the reflected light 412 as detected by the optical receiver 408. For example, proximity of the object may increase the level of reflected light 412 detected by the optical receiver 408. In another implementation, the optical proximity sensor 110(2) may use ToF techniques to measure a propagation time of the emitted light 410 from the optical emitter 406 to optical receiver 408 and determine a distance to the object. In yet another implementation, the optical proximity sensor 110(2) may use structured light techniques to determine proximity.

In another implementation, the optical emitter 406 may comprise a device, such as an LED used as a camera flash for operation of the image sensor 110(1), while the optical receiver 408 may comprise the light sensor 110(7). To minimize the users 102 perception of operation of the device, the duration of the emitted light 410 may be brief. For example, the emitted light 410 may be emitted in pulses having duration of less than 100 μs and with an interval of several hundred milliseconds or more between each pulse. As a result, instead of a flash the user 102 may instead see a dim glow or nothing at all from the optical emitter 406 when the emitted light 410 comprises otherwise visible wavelengths of light.

Figure 9:
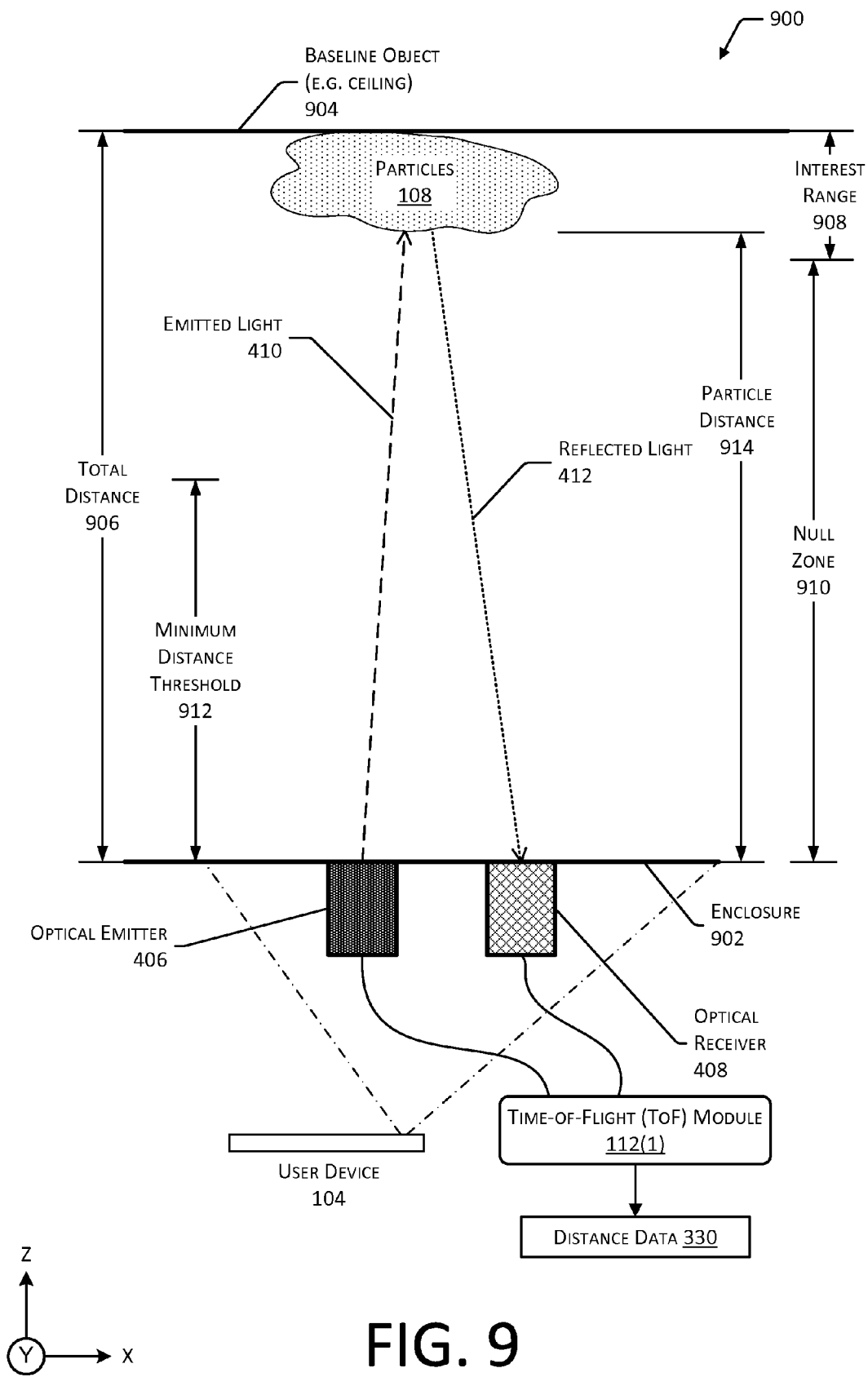
FIG. 9 illustrates a proximity sensor using time-of-flight to detect airborne particles.

FIG. 9 illustrates a scenario 900 in which an optical proximity sensor 110(2) uses time-of-flight (ToF) to detect airborne particles 108. As described above, the airborne particles 108 at a particular point or within a given volume may interact with the emitted light 410. This interaction may be detected at a distance. By using a ToF sensor to generate distance data 330 while the user device 104 is relatively stationary, changes to the distance data 330 over time may be indicative of airborne particles 108. For example, a cloud of smoke which accumulates at a ceiling may change the distance data 330 generated by the optical proximity sensor 110(2) as the emitted light 410 is reflected by a lower portion of the cloud which is closer to the optical proximity sensor 110(2).

In this scenario 900, the optical emitter 406 and the optical receiver 408 are configured to send emitted light 410 and receive reflected light 412 beyond an enclosure 902. For example, the optical emitter 406 and the optical receiver 408 may both be arranged on a front side of the user device 104. In this scenario, the user device 104 has been set facing up on a nightstand within a hotel room, such that the emitted light 410 from the optical emitter 406 is directed towards a baseline object 904 such as the ceiling. The baseline object 904 may comprise any other suitable object such as an architectural structure which is within the field-of-view of the optical proximity sensor 110(2) during operation.

During initial operation, the data processing module 112 determines a total distance 906 between the optical proximity sensor 110(2) and at least a portion of the baseline object 904. For example, an illustration here the total distance 906 is from the upper surface of the user device 104 to the ceiling 904.

An interest range 908 may be specified. The interest range 908 may be a fixed range or may be dynamically adjusted. The interest range 908 specifies a range of distance, which extends from the baseline object 904 towards the optical proximity sensor 110(2) on the user device 104. The interest range 908 delineates a range of distance within which changes may be indicative of airborne particles 108. For example, the interest range 908 may specify a distance of 50 centimeters (cm). Should an object be detected within the interest range 908, an alert or notification may be generated. The interest range 908 may be stored as the threshold data 336.

A null zone 910 may also be specified. The null zone 910 extends from the edge of the interest range 908 which is closest to the optical proximity sensor 110(2) to the optical proximity sensor 110(2) itself. A detected object having distance data 330 placing it within the null zone 910 may be disregarded. For example, should the user 102 move their hand over the user device 104, or an insect fly past the user device 104, the data processing module 112 may disregard this sensor data 114 as not being indicative of the particles 108. The null zone 910 may be stored as the threshold data 336.

In some implementations, a minimum distance threshold 912 may be specified that designates a distance beyond which an object may be considered a particle 108. For example, the minimum distance threshold 912 may specify 150 cm. Objects detected which have distance data 330 indicative of a distance of less than or equal to 150 cm from the optical proximity sensor 110(2) may be deemed to be non-particles 108, such as a hand of the user 102, an insect, and so forth. In comparison, objects detected which have distance data 330 indicative of a distance greater than 150 cm from the optical proximity sensor 110(2) may be deemed to be particles 108 or potentially be designated as particles 108. The minimum distance threshold 912 may be stored as the threshold data 336.

A particle distance 914 comprises distance data 330 indicative of a distance between the optical proximity sensor 110(2) and the particles 108. Continuing the example, smoke resulting from a fire may begin to accumulate at the ceiling 904 due to the higher temperature of the smoke laden air. Because the particles 108 are between the baseline object 904 and the optical proximity sensor 110(2), they reflect light 412 and result in distance data 330 indicative of the particle distance 914. As illustrated here, the particle distance 914 places a detected portion of the particles 108 within the interest range 908. As a result, the data processing module 112 may generate instructions for the user interface module 338 to generate user interface data 340 to play an audio sound such as a siren or take other action to notify the user 102, other parties such as emergency services, or both.

In some situations, the particles 108 may obscure or absorb the emitted light 410 resulting in a reduction or outright elimination of the reflected light 412. For example, black smoke may absorb the emitted light 410. As a result, the data processing module 112 may determine distance data 330 that is indicative of increased distance, or the data processing module 112 may detect a loss of signal when the reflected light 412 is no longer received by the optical receiver 408. In some situations, these indications alone or in combination with other sensor data 114 may be used to determine the presence or absence of particles 108.

The interaction between the emitted light 410 and the particles 108 may occur over a volume. To collect data over this volume, the ToF sensor or the ToF module 112(1) may be configured to integrate data over a period of time. For example, data received by the ToF sensor may be accumulated over time. The integration may occur at the ToF sensor, such as the analog domain, or the data may be integrated in a digital domain, such as by the ToF module 112(1). For example, integration in the analog domain may comprise extending the amount of time a detector accumulates a signal prior to readout. The ToF module 112(1) may be configured to determine the total distance 906 with regard to time, instead of or in addition to, distance.

The ToF sensor or the ToF module 112(1) may gate, integrate, or otherwise process the signals with respect to the time values. For example, the total distance 906 to the ceiling, which is the baseline object 904, may be 2 m, resulting in a propagation time of approximately 13.76 ns for the emitted light 410 from the optical emitter 406 to reach the ceiling and bounce back to the optical receiver 408. The interest range 908 may comprise a 30 cm volume extending from the ceiling, equivalent to a minimum round trip time of 11.696 ns. The ToF module 112(1) may use the optical receiver 408 to integrate reflected light 412 received during an interval from about 11.6 ns to 13.8 ns. As a result of the integration, the ToF module 112(1) may be more sensitive to particles 108 within the volume defined by the interest range 908. In other implementations, non-ToF methods such as structured light may sample or obtain a plurality of sample points within a given volume, range of distances, and so forth.

The distance data 330 may be processed to remove noise. For example, an overhead rotating fan may result in the total distance 906 changing every 100 ms as a fan blade moves in and out of the path of the emitted light 410. The data processing module 112 may be configured to filter out such noise from the sensor data 114.

In some implementations, one or more optical emitters 406 may be configured to generate a plurality of different wavelengths of emitted light 410. Likewise, one or more optical receivers 408 may be configured to detect the plurality of different wavelengths. Different wavelengths may be selected based on ambient lighting conditions, type of particles 108 to be detected, and so forth. For example, a near infrared emitted light 410 and a far infrared emitted light 410 may be used to characterize particles 108. Continuing the example, the characterization may be based on differences in optical scattering or other optical interactions between different sized particles 108 and their respective different wavelengths of light.

In other implementations, the structured light module 112(2) may be used instead of or in addition to the ToF module 112(1) to determine the distance data 330. Operational data processing module 112 and subsequent generation of user interface data 340 may be the same or similar to those described above with regard to the ToF module 112(1).

Figure 10:
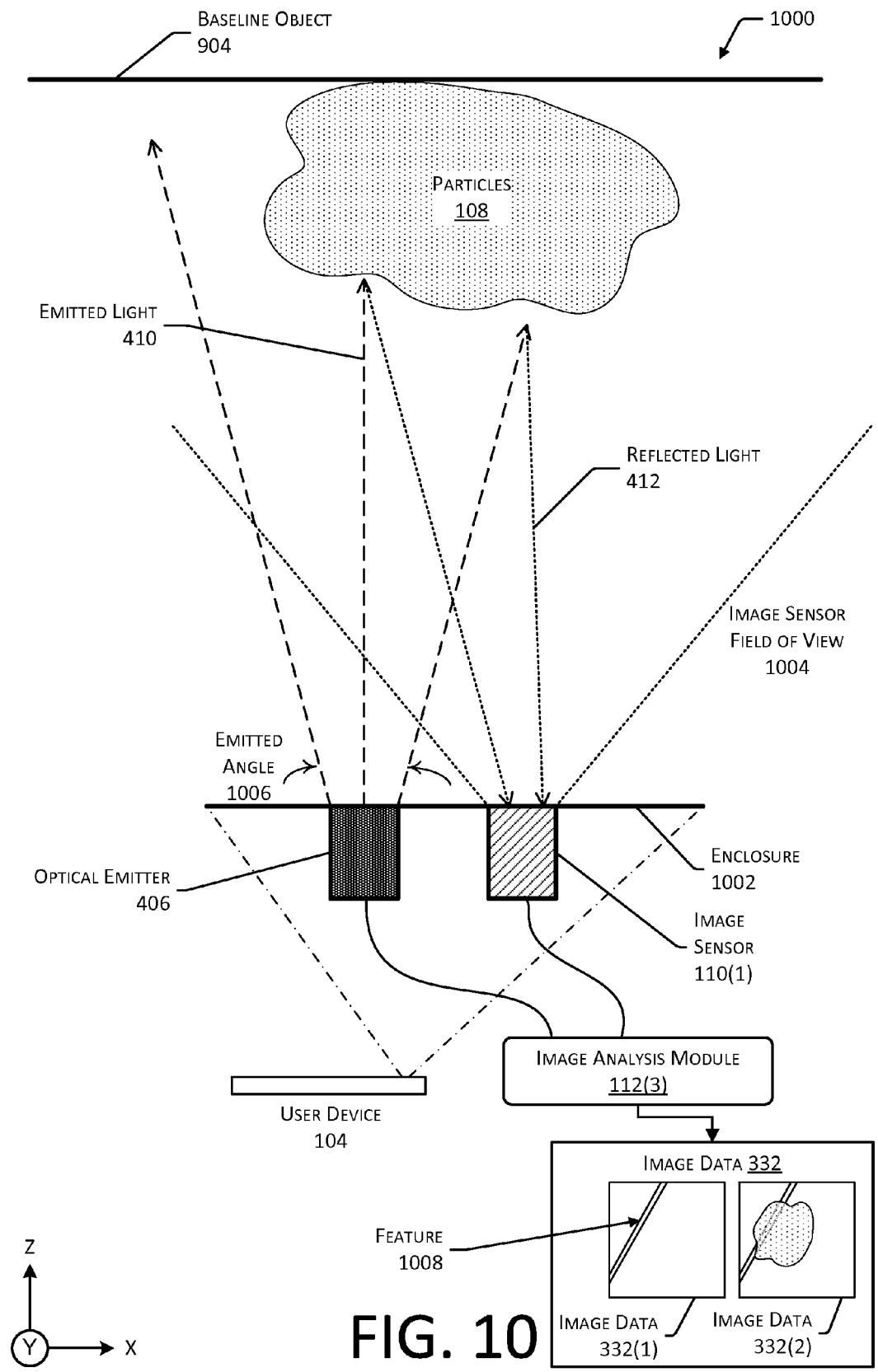
FIG. 10 illustrates an image sensor, such as a camera, configured to detect airborne particles.

FIG. 10 illustrates a scenario 1000 in which an image sensor 110(1) is configured to detect airborne particles 108. In this scenario 1000, the optical emitter 406 is configured to send emitted light 410 beyond an enclosure 1002, while an image sensor 110(1) is configured to gather image data 332 of a scene beyond the enclosure 1002. For example, the optical emitter 406 and the image sensor 110(1) may both be arranged on a front side of the user device 104. As described above, the optical emitter 406 may comprise a dedicated device, or may be used for other purposes, such as a camera flash.

As above with regard to FIG. 9, in this scenario, the user device 104 has been set facing up on a nightstand within a hotel room, such that the emitted light 410 from the optical emitter 406 is directed towards a baseline object 904 such as the ceiling. The baseline object 904 may comprise any other suitable object such as an architectural structure which is within the field-of-view of the optical proximity sensor 110(2) during operation.

The image sensor 110(1) has an angular field-of-view (FOV) 1004, which includes one or more objects in the scene such as the baseline object 904 and potentially particles 108. The optical emitter 406 may be configured to provide a beam of emitted light 410 having an emitted angle 1006 or beamwidth. For example, the image sensor FOV 1004 may have an angular field of view of about 120 degrees, while the emitted angle 1006, or beamwidth, may be about 30 degrees.

The optical emitter 406 is configured to generate a beam of emitted light 410, which traverses at least a portion of the image sensor FOV 1004. As particles 108 enter the beam of emitted light 410, reflected light 412 may be directed toward the image sensor 110(1). A portion of the image data 332 contains data about the portion of the beam which traverses a region of the image sensor FOV 1004 as well as other portions of the scene which are outside of the beam. By comparing information about the pixels corresponding to a region traversed by the beam with those corresponding to a region not traversed by the beam, the image analysis module 112(3) may dynamically adjust for ambient lighting conditions. Once suggested, information about the airborne particles 108 may be determined and used to generate sensor data 114. For example, should the beam be clearly visible in the acquired image data 332, the data processing module 112 may determine that the concentration of particles 108 is above a threshold value.

In some implementations, the image sensor 110(1) may look for changes between a plurality of images in the image data 332 which may be indicative of airborne particles 108. For example, one or more features 1008 in the image data 332 may be determined. The features 1008 may comprise architectural elements such as crown molding, light fixtures, pieces of art, decorative elements, elevation changes in a ceiling, changes in paint colors, printed wallpaper, and so forth. The features 1008 may have visible edges or contours, which may be determined by the image analysis module 112(3). First image data 332(1) acquired when the air is clear may show the features 1008 with edges being distinct. Second image data 332(2) acquired at a later time when the air is full of particles 108 may result in the features 1008 being obscured or the edges thereof becoming indistinct. Should the change in distinctness of the edges or other changes to the features 1008 between images be determined, the data processing module 112 may proceed to generate sensor data 114 that indicates a presence of airborne particles 108. In other implementations, other aspects of the image data 332 may be analyzed to look for changes. For example, a change in shape of the feature 1008, apparent movement between images, and so forth, may be used instead of or in addition to the techniques described above.

In some implementations, one or more of the different configurations and scenarios described above may be used in conjunction with one another. For example, the particle sensors 110(15) may be used in conjunction with the optical proximity sensors 110(2) and the image sensors 110(1) to gather information about airborne particles 108.

Illustrative Processes

Figure 11:
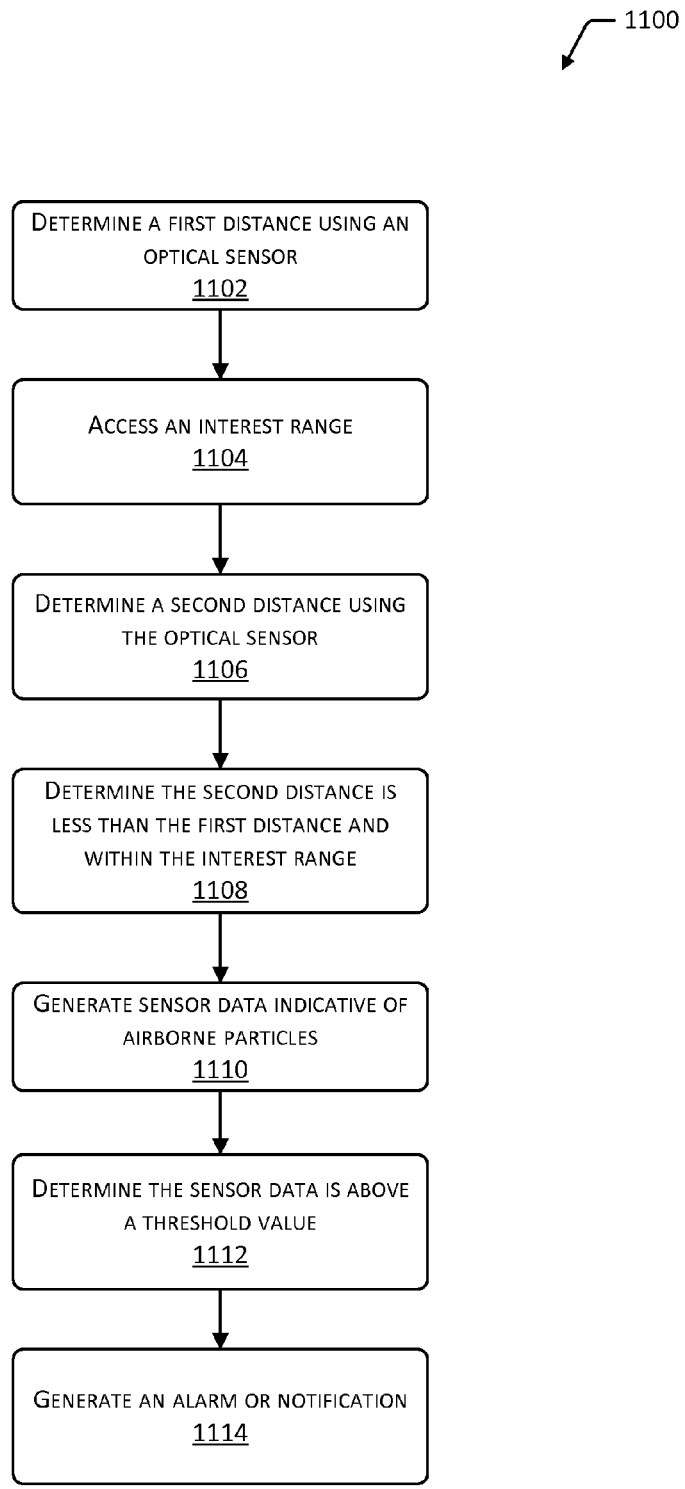
FIG. 11 illustrates a flow diagram of a process to use distance data, such as from the time-of-flight sensor, to detect airborne particles.

FIG. 11 illustrates a flow diagram 1100 of a process to use distance data 330 to detect airborne particles 108. As described above with regard to FIG. 9, distance data 330 may be generated by using optical sensors such as the optical proximity sensors 110(2), the 3-D sensors 110(13), and so forth. The optical sensors may use ToF, structured light, interferometry, or other techniques to determine the distance to an object.

Block 1102 determines a first distance using an optical sensor at a first time. For example, the total distance 906 may be determined. In some implementations, the first distance may be deemed beyond the minimum distance threshold 912. The optical sensor may be directed to measure a distance to a portion of a building. For example, the optical sensor may be directed to measure a distance to a ceiling of a room in which the device that contains the optical sensor is present.

As described above with regard to the ToF module 112(1), the determination of the distance data 330 may include emitting an optical pulse from an optical emitter 406. For example, the optical emitter 406 may comprise a laser that emits the emitted light 410. A reflection, refraction, fluorescence, and so forth, from an object resulting from the optical pulse is detected at a detector. For example the optical receiver 408 may receive reflected light 412. A propagation time for the optical pulse to travel from the optical emitter 406 to the object and back to the detector is determined. The distance data 330 may then be calculated using the propagation time. For example, the propagation time in seconds may be multiplied by the speed of light in air to determine the distance. In some implementations, the distance data 330 may be expressed in terms of time. For example, the propagation time, or a value based thereon, may be used as the distance data 330.

As described above with regard to the structured light module 112(2), the determination of the distance data 330 may include the emission of a structured light pattern from an optical emitter 406. For example, the structured light pattern may comprise a plurality of features in a predetermined arrangement projected from a holographic film illuminated by an LED. The structured light pattern may comprise a regular pattern such as a grid, a pseudorandom noise "speckle" pattern, and so forth. The pattern comprises one or more features at known locations relative to one another within the pattern. An image sensor 110(1) detects and acquires image data 332 of least a portion of the structured light pattern as reflected from the object. An apparent distance between at least a portion of the plurality of features within the image is determined. A distance to the at least a portion of the plurality of features may then be determined using the apparent distance in the image. For example, where the two features are very close to one another in the image, the object is very close, and where the two features are very far apart from one another in the image, the object is very far away.

Block 1104 accesses an interest range 908. In some implementations, the interest range 908 may comprise a range, extending from the first distance towards the optical sensor.

Block 1106 determines a second distance using the optical sensor at a second time. For example, the particle distance 914 may be determined.

Block 1108 determines that the second distance is less than the first distance and within the range specified by the interest range 908. For example, the particle distance 914 is less than the total distance 906 and within the range specified by the interest range 908.

Block 1110 generates sensor data 114 indicative of airborne particles 108 based at least in part on the change between the first distance and the second distance.

Block 1112 determines the sensor data 114 indicative of airborne particles 108 is above a threshold value. For example, the change in reflectivity may be above a threshold value, a change in distance data 330 may exceed a threshold percentage of variance, and so forth.

Block 1114 generates data indicative of an alarm comprising one or more of an audible output, visual output, or haptic output. The alarm may be presented using one or more of the output devices 202. In some implementations, at least a portion of the sensor data 114 may be sent to the computing device 120 or another device. For example, sensor data 114 may be sent to a public service access point maintained by an emergency services department of a local municipality.

In some implementations, the computing device 120 may provide report data 126 to the user device 104. For example, the report data 126 may comprise information acquired from a plurality of other user devices 104. In some implementations, the computing device 120 may provide additional processing resources to analyze the sensor data 114 to reduce or eliminate false alarms.

As described above, in some implementations, changes in the reflectivity of the object may be indicative of airborne particles 108. For example, the ceiling may grow very dark with black smoke or very white with light colored smoke. A first additional block determines a first reflectivity indicative of an intensity of reflected light resulting from light emitted during the first time. For example, the first reflectivity may indicate that the baseline object 904 is very reflective, such as a white ceiling. A second additional block determines a second reflectivity indicative of an intensity of reflected light resulting from light emitted during the second time. For example, the second reflectively may indicate that the quantity of the reflected light 412 has been significantly reduced indicating that the baseline object 904 has become less reflective or particles 108 have obscured the reflected light 412 from the optical receiver 408. A third additional block determines a reflectivity difference between the first reflectivity and the second reflectivity exceeds a threshold value. The generation of the sensor data 114 may further use the reflectivity difference. For example, a change in reflectivity exceeding 15% may be deemed to be indicative of airborne particles 108.

As described above with regard to FIG. 10, in some implementations, the image analysis module 112(3) may be used to generate sensor data 114. A first additional block may acquire a first image using the image sensor 110(1) at a third time. A second additional block may then acquire a second image at a fourth time. A third additional block processes the first image and the second image to determine an image change between the first image and the second image that is indicative of the airborne particles 108 exceeding a threshold value. For example, a change in apparent color may exceed a threshold value, the distinctness of an edge or other feature 1008 in the image may drop below a threshold value, and so forth. The generation of the sensor data 114 may further use the image change to determine presence, absence, or other information about the particles 108.

In one implementation, the processing of the first image and the second image may include analysis of one or more edges of the features 1008. A first additional block may determine, in the first image, an edge of a feature 1008 within a field-of-view 1004 of the image sensor 110(1). For example, the edge may comprise a change in elevation of the ceiling, portion of the doorframe, portion of a window, and so forth. A second additional block may determine in the second image and relative to the first image, one or more of the following: a decrease in sharpness of the edge of the feature 1008 resulting from the airborne particles 108, or an obscuration of at least a portion of the edge of the feature 1008 resulting from the airborne particles 108. For example, smoke may make the edges of the doorframe indistinct or may completely obscure at least a portion of the doorframe.

The data processing module 112 may determine whether the one or more sensors 110 have moved between or during acquisition of data. As described above, this movement may be determined by analyzing information from one or more of the sensors 110. A first additional block may determine, prior to the determination of the first distance, a first value indicative of one or more of orientation, acceleration, or rotation of the sensor 110 or the user device 104 to which it is coupled. For example, the magnetometer 110(12), the accelerometer 110(10), the gyroscope 110(11), the location sensor 110(14), and so forth, may be queried to determine whether the respective sensor 110 is motionless. A second additional block may determine, prior to the determination of the second distance, a second value indicative of one or more of orientation, acceleration, or rotation. A third additional block may determine whether the first value and the second value are within a threshold value of one another. For example, output from the magnetometer 110(12) may be within instrumentation drift associated with magnetometer 110(12) and thus not indicative of a change in orientation. In other implementations, similar techniques may be used to determine the user device 104 has remained relatively stationary between acquisitions of sensor data 114, such as successive images and so forth.

Based at least in part on the determination as to whether the first value and the second value are within a threshold value, the data processing module 112 may perform one or more actions. For example, upon determination that motion is taking place, the data processing module 112 may discard previously acquired sensor data 114 and begin gathering new information, such as a new total distance 906. In another example, upon determining that no motion has occurred, the data processing module 112 may generate an alarm responsive to the sensor data 114 exceeding one or more of the thresholds specified in threshold data 336.

Figure 12:
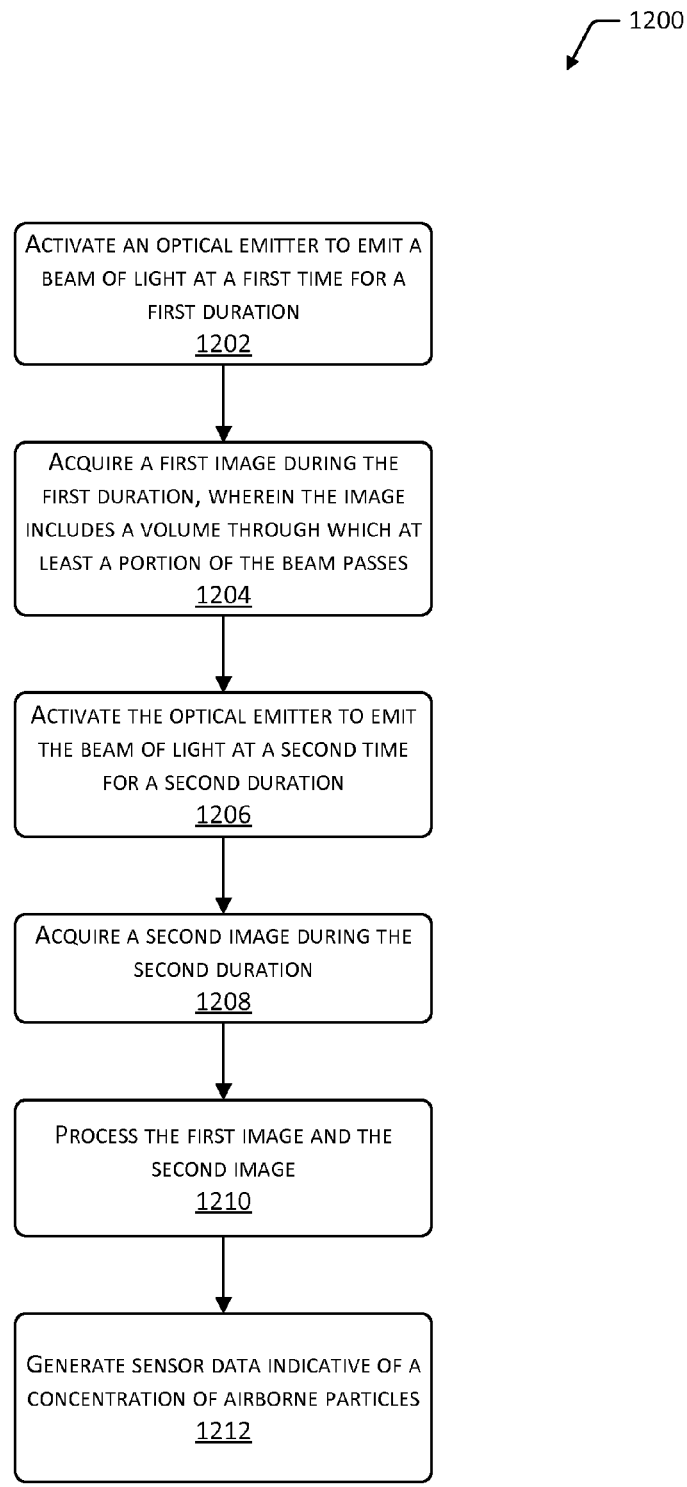
FIG. 12 illustrates a flow diagram of a process to use the image sensor to detect airborne particles.

FIG. 12 illustrates a flow diagram 1200 of a process to use the image sensor 110(1) to detect airborne particles 108. As described above with regard to FIG. 10, image data 332 comprising one or more images may be generated by the image sensor 110(1).

Block 1202 activates an optical emitter 406 (such as a light) to emit a beam at a first time for a first duration. As described above, the optical emitter 406 may be configured to generate emitted light 410 in one or more of wavelengths including, but not limited to, ultraviolet light, visible light, or infrared light. The duration of time for which the optical emitter 406 is active may be of a relatively short time. For example, the emitted light 410 may be emitted in pulses having duration of less than 100 μs and with an interval of several hundred milliseconds or more between each pulse. As a result, instead of a flash, the user 102 may instead see a dim glow or nothing at all from the optical emitter 406 when the emitted light 410 comprises otherwise visible wavelengths of light.

Block 1204 acquires a first image during the first duration. For example, the image sensor 110(1) may be configured to acquire image data 332 while the optical emitter 406 is active.

Block 1206 activates the optical emitter 406 (such as the light) to emit a beam of light at a second time for a second duration. Block 1208 acquires a second image during the second duration.

Block 1210 processes the image data 332 comprising the first image and the second image to determine a difference or change between the images that is indicative of a concentration of airborne particles 108 exceeding a threshold value. For example, the image analysis module 112(3) may analyze the image data 332 as described above to look for changes in color, edges, and so forth.

In one implementation, the beam of light may be configured to traverse a region corresponding to at least a portion of the image sensor FOV 1004. In some implementations, the emitted angle 1006, or the beamwidth, may be less than an angular width of the image sensor FOV 1004. In another implementation, the beam of light may be directed such that the beam occupies less than the entire image sensor FOV 1004. As a result, the images as expressed in the image data 332 include the beam as well as a portion which does not include the beam. Because the beam only traverses a portion of the image sensor FOV 1004 and thus only is in a portion of the image, a comparison between where the beam is and where the beam is not may be used to improve performance of the sensors 110. For example, this comparison may reduce interference or noise from ambient light or the objects in the image.

A first additional block may determine a baseline light level using pixels representative of portions of the images corresponding to a region not traversed by (or outside of) the beam. For example, the pixels corresponding to the region not traversed by the beam may be measured to determine an overall brightness. A second additional block may determine a signal light level using pixels corresponding to a region traversed by (or within) the beam. The generation of the sensor data 114 may comprise a comparison between the baseline light level and the signal light level. For example, the baseline light level may indicate a brightness of "5" while the signal light level may indicate a brightness of "250" that is visible to the image sensor 110(1). The beam may be visible due to a high concentration of airborne particles 108.

In another implementation, objects in the images may be used to determine information about the particles 108. A first additional block determines, in the first image, an edge of a feature 1008 within the image sensor FOV 1004 and a sharpness or blur value associated with that feature 1008. The feature 1008 may comprise a structure or picture that produces an edge in the image. An edge as depicted in an image may comprise a set of points at which image brightness exhibits a change above a threshold value. Edges may be formed by a change in a paint or pigment, physical structures, and so forth. For example, an edge of the doorframe or crown molding may be detected. In another example, the edge may comprise a line printed on wallpaper, a junction between two different colors of paint upon a wall, and so forth.

In one implementation, the OpenCV function "Canny" may be used to determine the edges. The "Canny" function implements the Canny Edge Detector, also known as the "optical detector" as developed by John F. Canny. With this technique, a Gaussian blur is applied to the image to reduce or eliminate speckles and noise. A gradient operator is applied for obtaining the gradients' intensity and direction. Non-maximum suppression determines if a given pixel is a better candidate for an edge than its neighbors. Hysteresis threshold is then used to find where edges begin and end. Other edge detection techniques may be used instead of, or in addition to, the Canny Edge Detector. For example, these techniques may include, but are not limited to: gradient based edge detection, Laplacian based edge detection, use of the Sobel operator, use of the Robert's cross operator, Prewitt's operator, Laplacian of Gaussian, and so forth.

In some implementations, sharpness may be defined in terms of the amount of blur present in the image or at a portion of the image. For example, the image analysis module 112(3) may be configured to quantify blur within an image using a variety of techniques. For example, H. Hu and G. de Haan describe one technique in their paper "Low cost robust blur estimator" as presented in the Proceedings of IEEE International Conference on Image Processing ICIP 2006, (pp. 617-620). Los Alamitos, USA: IEEE Society Press. With this technique, an input image is re-blurred with different blur radii, and a ratio between the multiple re-blurred images and the input image is calculated. A survey of other techniques is described in "Blur Detection Methods for Digital Images—A Survey" by R. Y. Landge and R. Sharma as presented in the International Journal of Computer Applications Technology and Research, Vol. 2, Issue 4, 495-498, 2013. In some implementations, at least one or more techniques may be used in conjunction with one another to determine the blur.

In another implementation, a change in sharpness may be determined based on a change in edge from one image to another. For example, the first image may include an edge detected using the Canny Edge Detector at a particular set of pixel coordinates. Continuing the second example, in the second image, the Canny Edge Detector may determine that no edge is present, or the Canny Edge Detector may determine properties of the edge have changed. As a result of this difference, the sharpness of the edge may be deemed to have decreased.

A second additional block determines, in the second image and relative to the first image, one or more of the following: a decrease in sharpness of the edge of the feature 1008, absence of at least a portion of the edge of the feature 1008, a change in shape or configuration of the edge of the feature 1008, or other changes. In some implementations, it may be assumed that changes in the appearance of the edge of the feature 1008 may be due at least in part to the presence to airborne particles 108.

Block 1212 generates sensor data 114 indicative of a concentration of airborne particles 108. In some implementations, data processing module 112 may further generate sensor data 114 that indicates the concentration of airborne particles 108 exceeds a threshold value as specified by the threshold data 336.

In some implementations, other sensors 110 may be used to generate the sensor data 114. For example, the optical proximity sensor 110(2) may be used as described above with regards to FIG. 9. A first additional block, the proximity sensor 110(2) may determine, at a third time, a first distance. A second additional block may use the proximity sensor 110(2) to determine, at a fourth time, a second distance. A third additional block determines the second distance is less than the first distance. The generation sensor data 114 may be based at least in part on the difference between the first distance and the second distance.

Additional blocks may be configured to determine the user device 104 has remained relatively stationary between acquisitions of sensor data 114. For example, the data processing module 112 may detect, prior to the acquisition of the first image by the image sensor 110(1), a first value indicative of one or more of orientation, acceleration, or rotation. The data processing module 112 may then detect, prior to the acquisition of the second image by the image sensor 110(1), a second value indicative of one or more of orientation, acceleration, or rotation. The data processing module 112 may designate the user device 104 as sufficiently stable for assessment of the particles 108 to proceed upon a determination that the first value and the second value are within a threshold value of one another. Continuing the example, where the user device 104 has remained stationary on a table between the acquisition of the first image and the second image, these images may be used to generate data about airborne particles 108. Should the data processing module 112 determine that the first value and the second value exceed the threshold value, such as where the user device 104 has been moved, previously acquired images or other data may be discarded and new sensor data 114 may be obtained. Continuing the example, the threshold value may specify that movement of the user device 104 is deemed to occur when orientation changes by more than 5 degrees, an acceleration of greater than 0.01 meters/second per second is exceeded, rotation exceeds 5 degrees, and so forth.

The processes discussed herein may be implemented in hardware, software, or a combination thereof. In the context of software, the described operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, floppy diskettes, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

What is claimed is:

1. A portable user device comprising:
a light source to emit a beam having a beamwidth;
a camera having an angular field-of-view which includes at least a portion of the beam and to acquire a first image and a second image;
a memory, storing computer-executable instructions; and
a hardware processor in communication with the light source, the camera, and the memory, wherein the hardware processor executes the computer-executable instructions to:
activate the light source to emit a beam at a first time for a first duration;
acquire the first image during the first duration;
activate the light source to emit a beam at a second time for a second duration;
acquire the second image during the second duration;
process the first image and the second image to determine, in the first image, an edge within the angular field-of-view, wherein the edge comprises a set of points at which image brightness exhibits a change above a threshold value and determine, in the second image and relative to the first image a decrease in sharpness of the edge indicative of a concentration of airborne particles exceeding a threshold; and
generate sensor data indicative of the concentration of the airborne particles exceeding the threshold value.

2. The portable user device of claim 1, determine, in the second image and relative to the first image an absence of at least a portion of the edge.

3. The portable user device of claim 1, wherein a beamwidth of the beam emitted at the first time or the beam emitted at the second time is less than the angular field-of-view of the camera; and
the computer-executable instructions further comprising instructions to:
determine a baseline light level using pixels of one or more of the first image or the second image corresponding to a region not traversed by the beam emitted at the first time;
determine a signal light level using pixels of the one or more of the first image or the second image corresponding to a region traversed by the beam emitted at the second time; and
the instructions to generate the sensor data further comprising instructions to:
compare the baseline light level and the signal light level.

4. The portable user device of claim 1, further comprising an optical proximity sensor to generate distance data to an object; and
the computer-executable instructions further comprising instructions to:
determine, using data from the optical proximity sensor, a first distance;
determine, using data from the optical proximity sensor, a second distance; and
the computer-executable instructions to generate the sensor data further comprising instructions to:
determine a difference between the first distance and the second distance.

5. The portable user device of claim 1, the computer executable instructions further comprising instructions to:
detect, prior to the acquisition of the first image, a first value indicative of one or more of orientation, acceleration, or rotation;
detect, prior to the acquisition of the second image, a second value indicative of the one or more of orientation, acceleration, or rotation; and
determine the first value and the second value are within a threshold range of one another.

6. A method comprising:
emitting a first optical pulse from an optical emitter;
detecting at an optical receiver one or more reflections of the first optical pulse from one or more objects;
determining a first propagation time indicative of a first time interval between the emitting of the first optical pulse and the detecting of the one or more reflections;
calculating a first distance to a baseline object using the first propagation time;
emitting a second optical pulse from the optical emitter;
detecting at the optical receiver one or more reflections of the second optical pulse from a second object;
determining a second propagation time indicative of a second time interval between the emitting the second optical pulse and the detecting the one or more reflections;
calculating a second distance to the second object using the second propagation time;
accessing a threshold value indicative of a change in distance;
determining the change in distance based on the first distance and the second distance;
determining that the change in distance is greater than or equal to the threshold value; and
generating data indicative of an alarm.

7. The method of claim 6, one or more of the calculating the first distance or the determining the second distance further comprises:
emitting, over a period of time, a plurality of pulses of light;
generating a plurality of values, each value indicative of detection of a reflection of one or more of the plurality of pulses; and
summing the plurality of values.

8. The method of claim 6, further comprising:
determining first reflectivity indicative of an intensity of reflected light resulting from light emitted by the optical emitter during the first time;
determining second reflectivity indicative of an intensity of reflected light resulting from light emitted by the optical emitter during the second time; and
determining that a difference between the first reflectivity and the second reflectivity exceeds a threshold value.

9. The method of claim 6, further comprising:
determining, prior to the calculating the first distance, a first value indicative of one or more of orientation, acceleration, or rotation of a device to which the optical receiver is coupled;
determining, prior to the calculating of the second distance, a second value indicative of the one or more of orientation, acceleration, or rotation of the device; and
determining the first value and the second value are within a threshold value of one another.

10. The method of claim 6, wherein the calculating one or more of the first distance or the second distance further comprises:
emitting a structured light pattern from the optical emitter, wherein the structured light pattern comprises a plurality of features in a predetermined arrangement;
detecting at an image sensor at least a portion of the structured light pattern as reflected from an object;
determining an apparent distance between at least a portion of the plurality of features; and
calculating the one or more of the first distance or the second distance to the at least a portion of the plurality of features using the apparent distance.

11. The method of claim 6, further comprising:
presenting the alarm comprising one or more of an audible output, visual output, or haptic output.

12. The method of claim 6, further comprising:
acquiring a first image using an image sensor at a third time;
acquiring a second image using the image sensor at a fourth time;
processing the first image and the second image to determine an image change between the first image and the second image; and
generating the data indicative of the alarm based on the image change and the second distance being within the change in distance.

13. The method of claim 12, the processing of the first image and the second image further comprising:
determining, in the first image, an edge within a field-of-view of the image receiver; and
determining, in the second image and relative to the first image, one or more of:
a decrease in sharpness of the edge; or
obscuration of at least a portion of the edge.

14. The method of claim 6, further comprising:
sending the data indicative of the alarm to a computing device;
receiving report data from the computing device, wherein the report data comprises information acquired from a plurality of optical sensors of other devices; and
generating output based at least in part on the report data.

15. A device comprising:
an optical sensor to determine distance from the device to an object;
one or more optical emitters to emit light of two or more wavelengths;
one or more optical receivers to detect the two or more wavelengths;
a memory, storing computer-executable instructions; and
a hardware processor in communication with the optical sensor and the memory, wherein the hardware processor executes the computer-executable instructions to:
  emit, via the one or more optical emitters, light at a first time for a first duration;
  acquire a first image during the first duration;
  emit, via the one or more optical emitters, light at a second time for a second duration;
  acquire a second image during the second duration;
  determine, in the first image, an edge within the angular field-of-view, wherein the edge comprises a set of points at which image brightness exhibits a change above a threshold value;
  determine, in the second image and relative to the first image, a decrease in sharpness of the edge indicative of a concentration of airborne particles exceeding a threshold;
  determine, at the first time, a first distance to a first object;
  determine, at the second time, a second distance to a second object that comprises a cloud of particles between the optical sensor and the first object; and
  generate data indicative of a change from the first distance at the first time to the second distance at the second time.

16. The device of claim 15,
wherein the wavelengths include one or more of infrared light, visible light, or ultraviolet light; and
the computer-executable instructions further comprising instructions to:
  determine first reflectivity indicative of an intensity of reflected light resulting from light emitted by the one or more optical emitters at a first wavelength;
  determine second reflectivity indicative of an intensity of reflected light resulting from light emitted by the one or more optical emitters at a second wavelength; and
  compare the first reflectivity and the second reflectivity with previously stored data to characterize one or more of the first object or the second object.

17. The device of claim 16, the optical sensor further comprising:
  circuitry to determine an elapsed time between emission of light by the one or more optical emitters and detection of the light by the one or more optical receivers; and
  circuitry to calculate one or more of the first distance or the second distance based on the elapsed time.

18. The device of claim 15, the computer executable instructions further comprising instructions to:
  detect, prior to the determination of the first distance, a first value indicative of one or more of orientation, acceleration, or rotation of the device;
  detect, prior to the determination of the second distance, a second value indicative of the one or more of orientation, acceleration, or rotation of the device; and
  determine the first value and the second value are within a threshold range of one another.

19. The device of claim 15, further comprising:
  a connector to electrically couple to a second device, wherein the second device comprises one or more of a smartphone, tablet, laptop, or set-top box; and
  a power supply to provide electrical power to the second device using the connector.

20. The device of claim 15, the computer-executable instructions further comprising instructions to:
  determine a baseline light level using pixels of one or more of the first image or the second image corresponding to a region not traversed by the beam emitted at the first time;
  determine a signal light level using pixels of the one or more of the first image or the second image corresponding to a region traversed by the beam emitted at the second time; and
  the instructions to generate the sensor data further comprising instructions to:
    compare the baseline light level and the signal light level.

* * * * *